(12) United States Patent
Van Bruggen et al.

(10) Patent No.: US 10,994,068 B2
(45) Date of Patent: May 4, 2021

(54) METHODS AND SYSTEMS FOR THE DETECTION AND REMOVAL OF PATHOGENS FROM BLOOD

(71) Applicant: Stichting Sanquin Bloedvoorziening, Amsterdam (NL)

(72) Inventors: Robin Van Bruggen, Amsterdam (NL); Astrid Elisabeth Visser, Amsterdam (NL)

(73) Assignee: Stichting Sanquin Bloedvoorziening, Amsterdam (NL)

(*) Notice: Subject to any disclaimer, the term of this patent is extended or adjusted under 35 U.S.C. 154(b) by 0 days.

(21) Appl. No.: 15/546,403

(22) PCT Filed: Jan. 26, 2016

(86) PCT No.: PCT/NL2016/050058
§ 371 (c)(1),
(2) Date: Jul. 26, 2017

(87) PCT Pub. No.: WO2016/122316
PCT Pub. Date: Aug. 4, 2016

(65) Prior Publication Data
US 2018/0264186 A1 Sep. 20, 2018

(30) Foreign Application Priority Data
Jan. 26, 2015 (EP) ................................ 15152486

(51) Int. Cl.
| | | |
|---|---|---|
| *C12N 11/02* | (2006.01) | |
| *A61M 1/36* | (2006.01) | |
| *G01N 33/569* | (2006.01) | |
| *G01N 33/555* | (2006.01) | |
| *C12Q 1/04* | (2006.01) | |
| *C12Q 1/10* | (2006.01) | |
| *C12Q 1/18* | (2006.01) | |
| *G01N 15/14* | (2006.01) | |
| *G01N 33/50* | (2006.01) | |
| *G01N 15/10* | (2006.01) | |

(52) U.S. Cl.
CPC ......... *A61M 1/3633* (2013.01); *A61M 1/362* (2014.02); *A61M 1/3675* (2013.01); *A61M 1/3679* (2013.01); *A61M 1/3693* (2013.01); *C12Q 1/04* (2013.01); *C12Q 1/10* (2013.01); *C12Q 1/18* (2013.01); *G01N 15/14* (2013.01); *G01N 33/5091* (2013.01); *G01N 33/555* (2013.01); *G01N 33/569* (2013.01); *A61M 1/3672* (2013.01); *A61M 2202/0429* (2013.01); *A61M 2205/75* (2013.01); *G01N 2015/1006* (2013.01); *G01N 2800/26* (2013.01)

(58) Field of Classification Search
None
See application file for complete search history.

(56) References Cited

U.S. PATENT DOCUMENTS

| 4,543,328 A | 9/1985 | Keller et al. |
|---|---|---|
| 7,789,847 B2 | 9/2010 | Gibbs et al. |
| 2013/0004937 A1 | 1/2013 | Yoshida et al. |

FOREIGN PATENT DOCUMENTS

| WO | 2012/075041 A2 | 6/2012 |
|---|---|---|
| WO | 2012/094671 A2 | 7/2012 |

OTHER PUBLICATIONS

Appendix: Microscopic Procedures for Diagnosing Malaria, CDC MMWR Surveillance Summaries, Jun. 8, 2007 / 56 (SS06); 39-40 (1-3). Retrieved from Internet May 20, 2016: http://www.cdc.gov/mmwr/preview/mmwrhtml/ss5606a3.htm.
Cardo, L.J., et al., Removal of Plasmodium Falciparum-Infected Red Blood Cells From Whole Blood by Leukoreduction Filters, Transfusion, 2009, 49:337-346.
Hament, J.-M., et al., Pneumococcal Immune Adherence to Human Erythrocytes, European Journal of Clinical Investigation, 2003, 33:169-175.
Hartmann, H., et al., Rapid Identification of *Staphylococcus aureus* in Blood Cultures by a Combination of Fluorescence In Situ Hybridization Using Peptide Nucleic Acid Probes and Flow Cytometry, Journal of Clinical Microbiology, 2005, 44(9):4855-4857.
Minasyan, H., Erythrocyte and Blood Antibacterial Defense, European Journal of Microbiology and Immunology, 2004, 4(2):138-143.
Yamaguchi, M., et al., *Streptococcus pneumoniae* Invades Erythrocytes and Utilizes Them to Evade Human Innate Immunity, PLOS ONE, 2013, 8(10), e77282:1-11.

*Primary Examiner* — Hope A Robinson
(74) *Attorney, Agent, or Firm* — Pillsbury Winthrop Shaw Pittman LLP

(57) ABSTRACT

The invention relates to methods and systems for removal of pathogens from blood or blood products. The invention further relates to methods and systems for treatment and diagnosis of infection in the blood and/or sepsis in a patient in need thereof.

12 Claims, 10 Drawing Sheets

METHODS AND SYSTEMS FOR THE DETECTION AND REMOVAL OF PATHOGENS FROM BLOOD

RELATED APPLICATIONS

This application is a U.S. National Stage of International Patent Application No. PCT/NL2016/050058, filed Jan. 26, 2016, entitled METHODS AND SYSTEMS FOR THE DETECTION AND REMOVAL OF PATHOGENS FROM BLOOD, and naming inventors Robin Van Bruggen and Astrid Elisabeth Visser, which published as International Patent Publication No. WO/2016/122316 on Aug. 4, 2016, and claims the priority of European patent application EP 15152486.5 filed Jan. 26, 2015. The entire content of the foregoing applications are incorporated herein by reference, including all text, tables and drawings.

FIELD OF THE INVENTION

The invention relates to the field of biology and medicine. In particular, the invention relates to methods and systems for the detection and removal of pathogens from blood or a blood component.

BACKGROUND OF THE INVENTION

Sepsis is a severe systemic inflammatory response to an infection. It results from an individual's immune system response and is associated with fever or hypothermia, rapid breathing, elevated heart rate, and/or edema and may lead to cardiovascular collapse and multiple organ failure. The pathophysiology of sepsis is due to the host inflammatory response rather than to the pathogen. Sepsis is characterized by the activation of multiple host defence mechanisms including the cytokine network, leukocytes, in particular neutrophils and monocytes, and the complement system. Sepsis is a major cause of morbidity and mortality in intensive care units, where it has a mortality rate of from 30 to 60%.

Sepsis occurs when an individual's immune system is unable to efficiently counteract an infection and remove pathogens from the blood stream resulting in an uncontrolled systemic inflammatory response. In most of the vertebrates platelets are responsible for binding and transporting pathogens in the blood to the reticulo-endothelial system (RES) where they are cleared from the blood. In humans and other higher primates, Red blood cells (RBCs) are responsible for binding and transporting immune complexes by using complement receptor 1 (CR1, CD35). CR1 interacts with all the opsonic complement fragments: C1q, mannose-binding lectin, C3b, and C4b. This way, once harmful particles such as pathogens are opsonized with complement fragments they are bound by RBCs. Once bound, the RBC transports the harmful particle to the sinusoids of the spleen and liver, where resident macrophages remove the RBC cargo, leaving the RBCs itself intact. This process is called immune-adherence clearance (IAC) and is critical for host defence and for continuous protection of the vascular wall from inflammation. Animal studies in primates and mice (using human CR1 transgenic mouse erythrocytes) have shown that immune adherence (IA) can be enhanced through CR1 expression. It has further been shown that when complement-opsonized pneumococci are injected intravenously (i.v.) with CR1+ mouse erythrocytes into wild type mice, they are cleared faster than opsonized pneumococci similarly injected with wild-type mouse erythrocytes and that the i.v. injection of pneumococci into CR1+ mice also results in more rapid clearance than in wild-type mice. Hence, immune adherence via CR1 on erythrocytes plays an important role in the clearance of immune complexes and pathogens.

Current medical treatment of sepsis mainly relies on antibiotics which is generally unsuccessful. An alternative to treatment with antibiotics is the purification of blood of a patient suffering from sepsis by apheresis. Apheresis is a process of withdrawal of blood from a donor or patient, whereby a part of the blood (e.g. plasma, leukocytes, platelets or RBC, etc.) is separated extracorporeally and retained and the remainder is re-transfused into the donor or patient. Different forms of apheresis are leukapheresis, plasmapheresis, thrombocytapheresis, etc. For instance, plasmapheresis is used to control the progress of sepsis. This process involves filtering blood through membranes to separate a patient's cells from their plasma so that pathogenic toxins as well as the host's inflammatory cytokines are removed, the plasma may then be replaced with plasma from healthy donors. A disadvantage of such method is that it is expensive, in part due to the need of donor plasma, and non-selective. The removal of host defence components may result in a risk of infection. In addition, there is a risk of an immune response of the host's immune system to donor plasma or its components. An alternative method is removing pathogenic toxins and cytokines from the blood by adsorption to compound that specifically bind thereto, such as antibodies against e.g. TNF-α and IL-Iβ and lipopolysaccharide (LPS). These methods are, however, costly due to the use of large amounts of specific antibodies and would need to be combined so that both pathogenic toxins and inflammatory cytokines are removed in order to sufficiently counteract sepsis. In addition, a further disadvantage of such methods is that pathogens are not removed from the blood but returned to the patient. Another method that does not have this disadvantage uses apheresis to remove pathogens from the blood by targeting the specific pathogen. An advantage of such method is that the removal of pathogens from the blood usually results in a quick inhibition of the host's inflammatory response. However, a major disadvantage of targeting the pathogen is that it is specific for one or a group of pathogens because the pathogen are captured using a ligand that is able to bind a specific pathogen. For instance, sepsis can be the result of infection by any kind of pathogen, i.e. bacteria, but also fungi, viruses, and parasites. For each type of pathogen multiple species or subgroups exist for which specific binding ligands need to be provided. This inevitably also means that it is necessary to diagnose the pathogen causing the infection before pathogen removal by apheresis can be performed. Since immediate treatment is essential in sepsis, diagnosis of the infecting pathogen may cause an unacceptable delay.

SUMMARY OF THE INVENTION

It is an object of the present invention to provide a method for removing pathogens from blood or from a blood component and to provide methods of treatment of bacterial infections in the blood, in particular of sepsis, by apheresis that overcome the disadvantages of the currently known methods.

The invention therefore provides a method for the removal of a pathogen from blood or a blood product comprising red blood cells, said method comprising:

separating said blood or blood product into at least two components, a first component comprising red blood cells (RBCs) and substantially free of white blood cells (WBCs) and platelets and at least a second component comprising WBCs and platelets and substantially free of RBCs;

contacting said first component with a filter comprising a non-specific RBC adhesion molecule binder thereby depleting said first component of RBCs that have bound at least one pathogen;

optionally combining said first component that is depleted of RBCs that have bound at least one pathogen and said at least second component.

Further provided is a method for the removal of a pathogen from blood of a patient in need thereof comprising:

withdrawing blood from said patient;

separating said blood into at least two blood components, a first component comprising red blood cells (RBCs) and substantially free of white blood cells (WBCs) and platelets and at least a second component comprising WBCs and platelets and substantially free of RBCs;

contacting said first component with a filter comprising a non-specific RBC adhesion molecule binder thereby depleting said first component of RBCs that have bound at least one pathogen;

optionally combining said first component that is depleted of RBCs that have bound at least one pathogen and said at least second component;

returning said first component that is depleted of RBCs that have bound at least one pathogen and said at least second component to said patient.

In a further aspect the invention provides a non-specific RBC adhesion molecule binder for use in a treatment of removing a pathogen from blood of a subject, said treatment comprising contacting a blood component comprising red blood cells and substantially free of white blood cells (WBCs) and platelets with a filter comprising said non-specific RBC adhesion molecule binder thereby removing RBCs that have bound at least one pathogen from said blood component.

In a further aspect the invention provides a non-specific red blood cell (RBC) adhesion molecule binder for use in a treatment of removing a pathogen from blood of a subject, said treatment comprising contacting a blood component comprising red blood cells (RBCs) and substantially free of white blood cells (WBCs) and platelets with a filter comprising said non-specific RBC adhesion molecule binder to allow binding of RBCs that have bound at least one pathogen to said non-specific RBC adhesion molecule binder, thereby removing said RBCs that have bound at least one pathogen from said blood component.

In a still further aspect the invention provides a use of a non-specific RBC adhesion molecule binder in the manufacture of a filter comprising said non-specific RBC adhesion molecule binder for a treatment of removing a pathogen from blood of a subject, said treatment comprising contacting a blood component comprising RBCs, which blood component is substantially free of WBCs and platelets, with a filter comprising said non-specific RBC adhesion molecule binder thereby removing RBCs that have bound at least one pathogen from said blood component.

In a still further aspect the invention provides a method for detecting pathogens in a sample of blood or of a blood product comprising red blood cells (RBCs), the method comprising:

i) contacting said sample with a support comprising a non-specific RBC adhesion molecule binder to allow binding of RBCs that have bound at least one pathogen to said binder;

ii) detecting the presence of RBCs that have bound at least one pathogen.

In a still further aspect the invention provides a method for identifying pathogens, such as sepsis-causing pathogens or infection-causing pathogens, in a sample of blood or of a blood product comprising red blood cells (RBCs), the method comprising:

i) contacting said sample with a support comprising a non-specific RBC adhesion molecule binder to allow binding of RBCs that have bound at least one pathogen to said binder;

ii) isolating RBCs that are bound to said support from said sample, preferably by removing cells and other components in said sample that have not bound to said binder;

iii) identifying the pathogen that is bound to said RBCs bound to said support.

In a still further aspect the invention provides a method for diagnosing an infection in the blood of a patient, the method comprising detecting pathogens and/or identifying pathogens in a sample of blood or a blood product comprising red blood cells (RBCs) of said patient with a method according to a method according to the invention.

In a still further aspect the invention provides a method for isolating and/or enriching pathogens from a sample of blood or of a blood product comprising red blood cells (RBCs), the method comprising:

i) contacting said sample with a support comprising a non-specific RBC adhesion molecule binder to allow binding of RBCs that have bound at least one pathogen to said binder;

ii) isolating RBCs that are bound to said support from said sample, preferably by removing cells and other components in said sample that have not bound to said binder.

In a still further aspect the invention provides a method for determining susceptibility for antibiotics of a pathogen, the method comprising, detecting pathogens and/or identifying pathogens in a sample of blood or a blood product comprising red blood cells (RBCs) with a method according to the invention isolating RBCs that are bound to said support from said sample;

contacting said isolated RBCs that are bound to said support with one or more antibiotic agents; and determining the growth of a functional activity of the pathogen.

In a still further aspect the invention provides a method for determining the presence of pathogens in a whole blood sample of an individual suffering from sepsis, suspected of suffering from sepsis or at risk of developing sepsis, the method comprising detecting the presence of red blood cells (RBCs) that have bound at least one pathogen using cytometry or microscopy.

Further provided is a system for removing a pathogen from blood or a blood product, wherein said system comprises a separation device for separating said blood or said blood product into at least a first component comprising red blood cells (RBCs) and being substantially free of white blood cells (WBCs) and platelets and at least a second component comprising white blood cells (WBCs) and platelets and being substantially free of red blood cells (RBCs), and wherein said system further comprises a filter device for depleting said first component of RBCs that have bound at least one pathogen, said filter device comprising a non-specific RBC adhesion molecule binder.

Moreover, the invention provides a pathogen bound RBC filter device for use in such system, wherein said pathogen bound RBC filter device is arranged for depleting a blood product of RBCs that have bound at least one pathogen, said filter device comprising a non-specific RBC adhesion molecule binder.

DETAILED DESCRIPTION

The invention relates to the detection and/or removal of pathogens from blood or from a blood component by targeting red blood cells (RBCs). The present inventors found that once RBCs have contacted and have bound a pathogen in the blood stream, the activation of adhesion molecules on the surface of these RBCs is increased. Without wishing to be bound by theory, it is believed that this mechanism contributes to clearance of pathogens from the blood by phagocytic monocytes and macrophages in the spleen and the liver. As described herein before, pathogens in the blood are quickly opsonized by complement fragments that bind to molecules on the surface of the pathogens. In humans and other primates RBCs bind complement opsonized pathogens and transport the pathogens to the liver and spleen. Here the pathogens are transferred from the RBCs to phagocytic cells whereby the RBCs remain intact and viable. The pathogens are subsequently taken up by phagocytic cells and degraded. Before the present invention it was believed that transfer of pathogens from RBCs to phagocytic cells is initiated once the phagocytic cells recognize the complement fragments of opsonized pathogens. However, the present invention demonstrates that RBCs change their phenotype after they bind complement opsonized pathogens via complement receptor CR1. More specifically the adhesion molecules on the cell surface of the RBCs are activated after binding of a complement opsonized pathogen to CR1. Without wishing to be bound by theory, it is believed that instead of, or in addition to, recognition of complement opsonized pathogens by phagocytic cells RBCs are able to interact with molecules expressed by phagocytic cells such as integrins, in particular complement receptor 3 (CR3). Hence, transfer of pathogens from RBCs to phagocytic cells in the spleen and liver is at least for a substantial part initiated by the interaction of RBCs adhesion molecules with the phagocytic cells.

RBCs express several adhesion receptors, although the expression and activity thereof is generally low so that RBCs are generally non-adhesive for other surface including endothelial cells and polymers such as those of leukocyte reduction filters. As a result, RBCs can be separated from WBCs and platelets using a leukocyte reduction filter, which adsorbs WBCs and platelets but not RBCs. Examples of adhesion molecules that are expressed on RBCs are CD44, ICAM-4, Lu/BCAM, CD147 and CD47. The present invention for the first time shows that RBCs that have bound opsonized pathogens via, mainly, complement receptor CR1 increase activation of at least adhesion molecules CD147, Lu/BCAM and ICAM-4 as a result of which RBCs become adhesive to polymer material, such as those leukocyte reduction filters. The present invention uses this principle to remove pathogens from the blood of a patient in need thereof or from a blood product, for instance blood obtained from a blood donor. Hence, now that the present invention provides the insight that RBCs after binding complement opsonized pathogens alter their phenotype, it has become possible to use this characteristic of RBCs to remove pathogens from blood or from a blood component. As a result of the activation of adhesion molecules on their cell surface, RBCs adopt a "sticky" phenotype. As a result thereof RBCs that have bound pathogens can be adsorbed to a material that is normally, i.e. when RBCs that have not bound pathogens or other immune complexes, not able to bind RBCs. Such material is herein referred to as a non-specific RBC adhesion molecule binder. This is opposed to a specific RBC adhesion molecule binder, e.g. a ligand that specifically binds CD147, ICAM-4 or Lu/BCAM, which specific binder is able to capture any RBC by binding to adhesion molecules expressed on the RBC surface.

A major advantage of the use of a filter comprising a non-specific RBC adhesion molecule binder as defined herein for the removal of pathogens from blood or from a blood product is that the same filter can be used to remove any type, e.g. but not limited to bacteria, fungi, viruses and parasites, and any species, e.g. but not limited to *S. aureus, S. typhimurium, E. coli, C. albicans, E. faecalis* and *B. subtilis*, of pathogen because the RBCs carrying the pathogens are adsorbed into or onto the filter material instead of the pathogens. Contrary, currently known methods target the pathogen and thus the filter or material needs to be specific for the pathogen that need to be removed from blood or a blood product. Further, contrary to known methods that merely inactivate pathogens or remove (foreign or the host's own) inflammatory mediators from the blood the methods of the present invention have a dual effect on sepsis. Not only is the pathogen load in the blood reduced, but also the host response is tempered because after the removal of pathogens the load of pathogen-derived foreign toxins is reduced in the circulation. Another advantage of the use of a filter comprising a non-specific RBC adhesion molecule binder as defined herein is that only RBC that have bound at least one pathogen are removed from the blood or blood product, so that the RBC not carrying a pathogen together with other blood components such as WBCs, platelets and plasma can be returned to a patient and no donor blood or plasma is needed. Yet another advantage of the use of such filter is that they can be prepared from generally available, inexpensive polymers.

A "non-specific RBC adhesion molecule binder" as used herein thus refers to a compound or material that interacts with adhesion molecules expressed on the surface of RBCs that can be used to distinguish RBCs that have bound at least one pathogen from RBCs that have not bound pathogens. A non-specific RBC adhesion molecule binder is able to adsorb a RBC only when the activation of adhesion molecules on the surface of a RBC is increased so that the RBC adopts a "sticky" phenotype. A non-specific RBC adhesion molecule binder as used herein therefore preferably binds to activated adhesion molecules expressed on RBCs. Said adhesion molecules are preferably activated by complement receptor 1 (CR1) expressed on the RBC which binds complement fragments that opsonize pathogens, such as C3b and C4b. A non-specific RBC adhesion molecule binder as used herein therefore preferably binds to CR1-activated adhesion molecules expressed on RBCs. Hence, a non-specific RBC adhesion molecule binder is preferably an activated RBC adhesion molecule binder, more preferably a CR1-activated RBC adhesion molecule binder. As used herein a "CR1-activated RBC adhesion molecule binder" thus refers to a material capable of binding adhesion molecules expressed on the surface of RBCs that are activated by CR1 after binding components and/or fragments of the complement system upon binding of pathogens to the RBC but not to adhesion molecules expressed on the surface of RBCs that have not been activated by components and/or fragments of the complement system binding to CR1. "Increased activation of adhesion molecules" as used herein can be determined by determining whether RBCs adopt a sticky phenotype as described herein, for instance by determining whether the RBCs bind to a BioR Blood filter of Fresenius Kabi (The Netherlands), as detailed in the Experimental part herein.

A non-specific RBC adhesion molecule binder is preferably a polymer. Alternatively, a non-specific RBC adhesion molecule binder is preferably a mixture of two or more polymers. Both synthetic and natural polymers are encompassed by the term "polymer" as used herein. Said polymer is for instance in the form of woven or non-woven polymer.

Preferred examples of polymers that can be used alone or in combination, in particular in a filter or beads according to the invention, are polyester, polyurethane, cellulose, nylon, nitrocellulose, polypropylene, polyethylene terephthalate (PET), polyimide (PI), polyvinyl alcohol (PVA), and polyvinylidene fluoride (PVDF). "Cellulose" as used herein refers to any form of cellulose, either natural or modified, including wood pulp cellulose, cotton cellulose, cellulose acetate, hydroxypropyl cellulose, methyl cellulose, and carboxymethyl cellulose.

Suitable methods to determine whether a material or compound, such as a polymer or mixture of two or more polymers, can be used as a non-specific RBC adhesion molecule binder and/or (complement-)activated RBC adhesion molecule binder are detailed in the Experimental part of this application. One such method comprises the preparation of support, such as a filter or beads, composed of the material and/or coated with the material. Pathogens can be opsonized by incubation with serum of AB+ healthy donors, followed by incubation with RBCs for e.g. 30 minutes, following a washing step. Subsequently, the sample comprising RBCs that have bound the opsonized pathogens are brought into contact with the support (e.g. filter or beads) composed of the material and/or coated with the material. The percentage and/or amount of pathogen-bound RBCs and RBCs that are not bound by pathogens in the sample can be assessed by flow cytometry prior to and after contacting the sample with the support. If the majority of the pathogen-bound RBCs (such as at least 75%) bind to the support and RBCs that are not bound to pathogens essentially do not bind to the support, the material is a non-specific RBC adhesion molecule binder according to the invention. In the methods and systems of the present invention preferably a support comprising a non-specific RBC adhesion molecule binder is used. Such support preferably comprises a filter, microfibers and microparticles, such as beads or microspheres, an array, glass slides and microscope slides. In one embodiment, such support may be essentially composed of said non-specific RBC adhesion molecule binder. In another embodiment, such support is coated with said non-specific RBC adhesion molecule binder. A blood sample, blood product or (first) component is preferably brought into contact with support comprising a non-specific RBC adhesion molecule binder incubation of the sample, product or component with said support. Alternatively, the sample, product or component is passed through the support, for instance if the support is a filter, or passed along the support, for instance if the support is a filter, a glass slides and/or microscope slide.

In the methods and systems of the present invention preferably a filter comprising a non-specific RBC adhesion molecule binder is used. The term "filter" as used herein refers to a device made of or comprising a non-specific RBC adhesion molecule binder and is used to adsorb RBCs that have bound at least one pathogen passing through or along the filter. Suitable filters can be prepared from polymers such as polyester, polyurethane, cellulose, nylon, nitrocellulose, polypropylene, polyethylene terephthalate (PET), polyimide (PI), polyvinyl alcohol (PVA), and polyvinylidene fluoride (PVDF). "Cellulose" as used herein refers to any form of cellulose, either natural or modified, including wood pulp cellulose, cotton cellulose, cellulose acetate, hydroxypropyl cellulose, methyl cellulose, and carboxymethyl cellulose. However, commercially available filters can also be used in the methods and system of the present invention. Preferred examples include, but are not limited to, nitrocellulose filters and leukocyte reductions filters. A particularly preferred filter is a leukocyte reduction filter. Leukocyte reduction filters are well known in the art, i.e. they are used for the removal of white blood cells (leukocytes) from blood or blood products. Such leukocyte reduction filters can be used in the methods of the present invention because the RBCs and WBCs and platelets are separated before the blood component comprising RBCs are passed through or along a filter. Examples of commercially available leukocyte reduction filters and nitrocellulose filters that can suitably be used in the methods and systems of the invention are known to the skilled person. An example of suitable leukocyte reduction filters are the BioR Blood filters of Fresenius Kabi, The Netherlands. A particularly preferred leukocyte reduction filter used as a filter comprising non-specific RBC adhesion molecule binder in accordance with the invention are BioR Blood filters of Fresenius Kabi (The Netherlands), in particular the BioR plus filter, BioR max filter and BioR mini filter.

In another embodiment of the methods and systems of the present invention preferably beads comprising a non-specific RBC adhesion molecule binder is used. Such beads are preferably essentially composed of or coated with a non-specific RBC adhesion molecule binder according to the invention, preferably a polymer or a mixture of two or more polymers. Suitable examples of beads are silica beads, polymer beads, including beads of polymers such as polyester, polyurethane, cellulose, nylon, nitrocellulose, polypropylene, PET, PI, PVA, and PVDF, magnetic beads, paramagnetic beads, fluorescently labelled beads, and the like. Preferably beads are suitable for use in flow cytometry detection methods. Examples of suitable beads are DYNABEADS® (Thermo Fisher Scientific) and CYTOSPHERES® (Beckman Coulter). Beads used as support in accordance with the inventions typically have a diameter of 10 μm or smaller, such as 25 nm to 10 μm.

Methods to determine whether a compound or material is able to distinguish RBCs that have bound at least one pathogen from RBCs that have not bound pathogens are known to a person skilled in the art. In the Experimental part described herein an example of such a method is described. This method uses control RBCs and RBCs that have been incubated with and are thus binding labelled pathogen such as GFP-expressing *S. aureus* which are subsequently contacted with the compound or material. The RBCs that have been incubated with pathogen may firstly be analysed by, e.g., FACS to determine the immune complex (IC) binding percentage. After the compound or material has been contacted with the control RBCs and RBCs that have been incubated with pathogen all non-sticking RBCs are obtained by washing the compound or material and yet again the RBC fractions are analysed by, e.g., FACS to determine the IC binding percentage. If a compound or material is able to distinguish RBCs that have bound at least one pathogen from RBCs that have not bound pathogens the IC binding percentage will be reduced.

As used herein the term "RBCs that have bound at least one pathogen" refers to RBC with at least one pathogen bound to their surface, preferably via a receptor of the complement system expressed on the cell surface of the RBC, such as complement receptor 1 (CR1). The term "pathogen" as used herein includes but is not limited to bacteria, viruses, fungi, parasites and protozoa that are able to infect an individual, in particular a human. The methods and systems of the invention are effective in removing all pathogens that are able to be bound by RBCs from blood or a blood component because the methods and systems do not target the pathogen but the RBCs that have bound at least one pathogen. For example, the methods and systems are effective in removing Gram-negative and Gram-positive bacteria. Examples of pathogenic bacteria that may cause infections in humans or animals that can be removed from the blood or a blood component with the methods of the invention include, but are not limited to, *Listeria, Escherichia, Chlamydia, Rickettsia, Mycobacterium, Staphylococcus, Streptococcus, Pneumococcus, Meningococcus, Klebsiella, Pseudomonas, Legionella, Diphtheria, Salmonella, Vibrio, Clostridium, Bacillus, Yersinia*, and *Leptospira* bacteria. Examples of pathogenic viruses that may cause infections in humans or animals that can be removed from the blood or a blood component with the methods of the invention include, but are not limited to, A, B or C hepatitis, herpes virus (for instance VZV, HSV-I, HAV-6, HSV-II, CMV, Epstein Barr-virus), adenovirus, influenza virus, flaviviruses, echovirus, rhinovirus, coxsackie virus, coronavirus, respiratory syncytial virus (RSV), rotavirus, Morbillivirus, rubella virus, parvovirus, vaccinia virus, HTLV virus, dengue virus, papillomavirus, poliovirus, rabies virus and human immunodeficiency virus (HIV virus; e. g., type I and II). Examples of pathogenic fungi that may cause infections in humans or animals that can be removed from the blood or a blood component with the methods of the invention include, but are not limited to, *Candida* (e.g., *albicans, krusei, glabrata, tropicalis*), *Aspergillus* (e.g., *fumigatus, niger*), *Cryptococcus neoformans, Histoplasma capsulatum,* Mucorales, *Blastomyces dermatitidis, Paracoccidioides brasiliensis*, and *Coccidioides immitis*. Examples of pathogenic parasites that may cause infections in humans or animals that can be removed from the blood or a blood component with the methods of the invention include, but are not limited to, *Entamoeba histolytica, Plasmodium* (e.g. *falciparum, vivax*), *Entamoeba, Giardia, Balantidium coli, Acanthamoeba, Cryptosporidium, Pneumocystis carinii, Babesia microti, Trypanosoma* (e.g. *brucei, cruzi*), *Leishmania* (e.g. *donovani*), and *Toxoplasma gondii*.

Bacterial pathogens, in particular gram-positive bacteria, are the most frequent cause of sepsis, although sepsis resulting from an infection with fungi is also considerable. Specific pathogens that are associated with the occurrence of sepsis are *Staphylococcus* species, in particular *Staphylococcus aureus*, Enterobacteriaceae, in particular *Escherichia coli, Streptococcus pneumoniae* (9%), *Klebsiella* species (6%), *Enterococcus* species, *Candida* spp, e.g. *Candida albicans, Pseudomonas* spp, *Haemophilus* influenza. The methods of the invention are particularly suitable for treating sepsis. Therefore, preferably a method of the invention comprises removal of gram-positive bacteria or fungi, more preferably selected from the group consisting of *Staphylococcus aureus, Escherichia coli, Bacillus subtilis, Enterococcus faecalis, Salmonella typhimurium, Candida albicans, Staphylococcus epidermidis, Serratia marcescens, Streptococcus pneumoniae, Haemophilus influenza, Streptococcus pyogenes, Klebsiella pneumoniae, Bacillus cereus, Bacillus thuringiensis, Enterobacter cloacae, Morganella morganii, Proteus mirabilis, Pseudomonas fluorescens, Salmonella cholerae*-suis, *Streptococcus dysgalactiae, Streptococcus bovis*. Particularly preferred methods of the invention comprise the removal of *Staphylococcus aureus, Salmonella typhimurium, Escherichia coli, Candida albicans, Enterococcus faecalis* and *Bacillus subtilis* from blood or a blood product.

The term "blood" as used herein refers to whole blood of a subject, preferably a human. Said whole blood optionally comprises compounds that are added to the blood or a component thereof when carrying out a method according to the invention, such as a anti-coagulant. The term "blood component" as used herein refers to any component that is separated from whole blood, including blood treated with an anti-coagulant, for instance white blood cells (WBCs) and platelets, plasma, RBCs, platelets or combinations thereof. The terms "white blood cells", "platelets" and "red blood cells" are known to the skilled person. WBCs are also referred to as leukocytes and are the cells of the immune system involved in defending the body against infectious organisms and foreign substances, which include neutrophils, monocytes and macrophages, eosinophils, basophils and lymphocytes, i.e. T cells, B cells and natural killer cells. RBCs are also referred to as erythrocytes and are cells that lack a nucleus and are mainly involved in transporting oxygen through the circulatory system. Platelets are also referred to as thrombocytes and are blood cells that have no nucleus. The term "blood product" as used herein refers to a product that comprises one or more blood components and/or whole blood. Said blood product preferably comprises RBCs. In a further embodiment, a blood product comprises RBCs and WBCs. More preferably RBCs, WBCs and platelets. An example of a blood product is a blood sample obtained from a blood donor, e.g. after it is processed for storage and thus for instance containing an anti-coagulant, and/or an additive solution such as, but not limited to, SAGM, AS-1, AS-3, AS-5, AS-7, PAGGSM and E-Sol.

The term "substantially free of WBCs and platelets" as used herein with respect to a component or a first component comprising RBCs and substantially free of WBCs and platelets refers to a blood component derived from blood or a blood product that has been treated to separate WBCs and platelets from RBCs. The term includes the presence of WBCs and platelets at the level of leukodepleted RBC units ($<15 \times 10^6$/L) and the presence of WBCs and platelets at a low level. As used herein "low level" with respect to cells or platelets refers to <10% of the starting value of the respective cells or platelets in the untreated blood or blood product. Hence, preferably a blood component that is substantially free of WBCs and platelets comprises at most 10% of the WBCs and platelets present in the blood or blood product from which the blood component is derived before the WBCs and platelets are separated from the RBCs, for instance using one of the techniques described herein such as centrifugation, counterflow centrifugation elutriation, size filtration, affinity chromatography or a combination thereof. More preferably, a blood component that is substantially free of WBCs and platelets comprises at most 5%, more preferably at most 4%, more preferably at most 3%, more preferably at most 2%, more preferably at most 1% of the WBCs and platelets present in the blood or blood product before WBCs and platelets, and RBCs are separated. Further, a (first) component comprising RBCs and substantially free of WBCs and platelets preferably comprises at least 90% of the total RBCs, i.e. both RBCs that have bound at least one pathogen and RBCs that have not bound a pathogen, present in the blood or blood product from which the blood component is derived before the WBCs and platelets on the one hand, and RBCs on the other hand therein are separated. More preferably, said component comprises at least 90% of the total RBCs, at least 95% of the total RBCs, at least 96% of the total RBCs, at least 97% of the total RBCs, at least 98% of the total RBCs, at least 99% of the total RBCs present in the blood or blood product from which the blood component is derived before the WBCs and platelets, and RBCs therein are separated. Hence, a component comprising RBCs and substantially free of WBCs and platelets preferably comprises at most 10%, preferably at most 5%, of the WBCs and platelets and at least 90%, preferably at least 95%, of the total RBCs present in the blood or blood product from which the component is derived before the WBCs and platelets and RBCs therein are separated. Such component comprising RBCs and essentially free of WBCs and platelets, is herein also briefly referred to as a "component comprising RBCs".

Similarly, the term "substantially free of RBCs" as used herein with respect to a component or a second component comprising WBCs and platelets and substantially free of RBCs refers to a blood component derived from blood or a blood product that has been treated to separate WBCs and platelets from RBCs. The term includes the complete absence of RBCs and the presence of RBCs at a low level. Preferably a blood component that is substantially free of RBCs comprises at most 10% of the RBCs present in the blood or blood product from which the blood component is derived before the WBCs and platelets and RBCs therein are separated, for instance using one of the techniques described herein such as centrifugation, counterflow centrifugation elutriation, size filtration, affinity chromatography or a combination thereof. More preferably, a blood component that is substantially free of RBCs comprises at most 5%, more preferably at most 4%, more preferably at most 3%, more preferably at most 2%, more preferably at most 1% of the RBCs present in the blood or blood product before WBCs and platelets, and RBCs are separated. Further, at least one (second) component comprising WBCs and platelets and substantially free of RBCs preferably comprises at least 90% of the total WBCs and platelets present in the blood or blood product from which the blood component is derived before the WBCs and platelets and RBCs therein are separated. More preferably, said component comprises at least 90% of the total WBCs and platelets, at least 95% of the total WBCs and platelets, at least 96% of the total WBCs and platelets, at least 97% of the total WBCs and platelets, at least 98% of the total WBCs and platelets, at least 99% of the total WBCs and platelets present in the blood or blood product from which the blood component is derived before the WBCs and platelets and RBCs therein are separated. Hence, a component comprising WBCs and platelets and substantially free of RBCs preferably comprises at most 10%, more preferably at most 5%, of the RBCs and at least 90%, more preferably at least 95%, of the WBCs and platelets present in the blood or blood product from which the component is derived before the WBCs and platelets and RBCs therein are separated. Such component comprising WBCs and platelets which is essentially free of RBCs, is herein also briefly referred to as a "component comprising WBCs and platelets".

The amount of RBCs, WBCs and/or platelets in blood, a blood product or a blood component can for instance be determined by taking a sample from the initial blood or blood product and the blood component and determining the concentration of RBCs, WBCs and/or platelets, for instance per ml, by flow cytometry after appropriate labelling or staining of the RBCs, WBCs and/or platelets using methods known to the skilled person or after analysis on a hematology analyser. If the concentration of RBCs, WBCs and/or platelets in the blood or blood product and in the blood component(s) and the volume of the blood or blood product and the blood component(s) is determined, the percentage of RBCs, WBCs and/or platelets present in the blood or blood product before separation of RBCs and WBCs and platelets that is present in a blood component can be determined.

In order to remove pathogens from blood or a blood product comprising said pathogen in accordance with the present invention, WBCs and platelets on the one hand and RBCs on the other hand first have to be separated substantially. Hence, a method of the invention comprises separating the blood or blood product into at least two components, a first component comprising RBCs, which is substantially free of WBCs and platelets, and at least one second component comprising WBCs and platelets, which is substantially free of RBCs. RBCs, and WBCs and platelets can be separated using any method known in the art. Examples of such methods are centrifugation, counterflow centrifugation elutriation, size filtration, affinity chromatography or a combination of these techniques. Optionally said separation step results in additional components such as a component comprising platelets and/or a component comprising plasma. Preferably, separation of blood or blood product into at least two components comprises centrifugation of the blood or blood product. Conventional blood collection and apheresis methods typically utilize differential centrifugation methods for separating blood into various blood components. In such centrifugation, blood or blood product is circulated through a container which is rotated at high rotational speeds. Rotation of the container results in a centrifugal force. The centrifugal field generated upon rotation separates particles, in particular cells and platelets, suspended in the blood sample into components based on their density. A blood sample is typically separated into phases comprising a highest density phase comprising RBCs, an intermediate density phase comprising platelets and WBCs and platelets and a lowest density phase comprising plasma. The first component comprises pathogen-bound RBCs and is thus further processed to remove said pathogens. The second component comprising WBCs and platelets and optionally further blood (product) derived components can be preferably led to a container where they are stored during further processing of the first component comprising RBCs.

In order to remove pathogens from the first component comprising RBCs, said first component is contacted with a filter comprising a non-specific RBC adhesion molecule binder. Said first component comprising RBCs is preferably contacted with the filter by flowing the component and/or RBCs through and/or along the filter. That way, RBCs that have bound at least one pathogen are adsorbed onto the material of the filter, i.e. the non-specific RBC adhesion molecule binder. RBCs that have not bound at least one pathogen, are not adsorbed to the filter material but flow through and/or along the filter. This way, the first component is depleted of RBCs that have bound at least one pathogen. Blood, a blood product or a component "depleted of RBCs that have bound at least one pathogen" as used herein refers to blood, a blood product, or a component from which the majority of the RBCs that have bound at least one pathogen are removed. The number of pathogens is preferably reduced to an amount that can be taken care of by the patient's immune system. Preferably at least 50%, more preferably at least 60%, more preferably at least 70%, more preferably at least 80%, more preferably at least 90% of the RBCs that have bound at least one pathogen are removed. Most preferably at least 95% of the RBCs that have bound at least one pathogen are removed from said blood component. RBCs that have bound at least one pathogen adsorbed onto the filter material are preferably discarded, optionally after inactivating the pathogen for instance using ultraviolet (UV) light or heat.

Optionally, an anticoagulant agent is added to the blood or blood product, preferably before the WBCs and platelets and RBCs of the blood or blood product are separated. Non-limiting examples of anticoagulants are heparin, warfarin, dicumarol, EDTA, fluoride, and citrate solutions. Therefore, the blood or blood product is preferably treated with an anticoagulant selected from the group consisting of heparin, warfarin, dicumarol, EDTA, fluoride, and citrate solutions.

A method of the invention further optionally comprises combining the first component that is depleted of RBCs that have bound at least one pathogen, the second component comprising WBCs and platelets and optional further components. Hence, the first component that is depleted of RBCs that have bound at least one pathogen can be either collected into a container before further processing or led into the container comprising the second component comprising WBCs and platelets and optionally further components. Blood, a blood product or a blood component from which pathogens have been removed using a method of the invention is herein also referred to as processed blood, a blood product or a blood component or blood, a blood product or a blood component processed in accordance with the invention. The first component that is depleted of RBCs that have bound at least one pathogen, the second component comprising and optional further components comprising e.g. plasma and/or platelets may contain residual pathogens that were not bound to RBCs in the blood or blood product processed in accordance with the invention. Hence, after combining the first component that is depleted of RBCs that have bound at least one pathogen, the second component and optional further components residual pathogens may be present. However, the fraction of non-bound pathogens to pathogens bound to RBCs in blood is typically low enough for a patient's own immune system to remove these residual pathogens once the processed blood, blood product or blood component is returned to the patient.

A method of the invention is particularly suitable for the removal of a pathogen from blood of a patient in need thereof, such as a patient suffering from an infection, or sepsis or a patient at risk of developing sepsis. Provided is therefore a method for the removal of a pathogen from blood of a patient in need thereof, comprising:

removing blood from said patient;

separating said blood into at least two blood components, a first component comprising red blood cells (RBCs) and a second component comprising white blood cells (WBCs) and platelets;

contacting said first component with a support, preferably a filter, comprising a non-specific RBC adhesion molecule binder thereby depleting said first component of RBCs that have bound at least one pathogen;

returning said first component that is depleted of RBCs that have bound at least one pathogen and said second component. Said method preferably comprises allowing binding of RBCs that have bound at least one pathogen to said non-specific RBC adhesion molecule binder. Said non-specific RBC adhesion molecule binder is preferably a polymer or a mixture of two or more polymers, more preferably a polymer. Removal of blood from a patient can be performed using a conventional apheresis needle. The methods and system of the present invention are both usable with single and dual needle configurations. In a single needle configuration, one needle is used for both removal of blood from a patient and for returning processed blood or blood components to the patient. In a dual need configuration a first needle is used for removing blood from a patient and a second needle is used for returning processed blood or blood components to the patient.

Further provide is the use of a non-specific RBC adhesion molecule binder in the manufacture of a support, preferably a filter, comprising said non-specific RBC adhesion molecule binder for a treatment of removing a pathogen from blood of a subject, said treatment comprising contacting a blood component comprising RBCs, which blood component is substantially free of WBCs and platelets, with said filter comprising said non-specific RBC adhesion molecule binder thereby removing RBCs that have bound at least one pathogen from said blood component. Said treatment preferably comprises allowing binding of RBCs that have bound at least one pathogen to said non-specific RBC adhesion molecule binder. Said non-specific RBC adhesion molecule binder is preferably a polymer or a mixture of two or more polymers, more preferably a polymer. Said treatment is further preferably for use, but not limited to, in the treatment of sepsis or a developing sepsis.

Also provided is a non-specific RBC adhesion molecule binder for use in a treatment of removing a pathogen from blood of a subject, said treatment comprising contacting a blood component comprising red blood cells and substantially free of white blood cells (WBCs) and platelets with a support, preferably a filter, comprising said non-specific RBC adhesion molecule binder thereby removing RBCs that have bound at least one pathogen from said blood component. Said treatment preferably comprises allowing binding of RBCs that have bound at least one pathogen to said non-specific RBC adhesion molecule binder. Said non-specific RBC adhesion molecule binder is preferably a polymer or a mixture of two or more polymers, more preferably a polymer. Said treatment is further preferably for use in the treatment of an infection in the blood of a patient, of sepsis or of a developing sepsis. As used herein "a developing sepsis" refers to a condition wherein pathogens are present in blood of a patient but the patient does not yet show clinical signs of sepsis, and/or has not yet been diagnosed with sepsis.

Treatment of sepsis is preferably a continuous treatment. Thus, a preferred method of the invention for treating sepsis comprises continuously removing blood from the patient, continuously separating said blood into at least two components, a first component comprising RBCs and substantially free of WBCs and platelets and a second component comprising WBCs and platelets, and substantially free of RBCs continuously passing said first component over a filter comprising a non-specific RBC adhesion molecule binder and continuously returning said at least two components to the patient, whereby said first component is depleted of RBCs that have bound at least one pathogen. Said at least two components, whereby said first component is depleted of RBCs that have bound at least one pathogen, are preferably combined before being returned to the patient. Such continuous treatment preferably comprises a dual needle configuration. Said continuous treatment is preferably continued until a sufficient amount of RBCs that have bound at least one pathogen is removed from the patients blood until sepsis is effectively treated. The duration of a treatment whereby the whole of a patient's blood is treated may for instance be between 4 and 6 hours, e.g. approximately 5 hours.

Alternatively, said treatment is performed cyclically. In this embodiment of the invention, blood is removed from the patient in blood draw cycles. Blood removed in each cycle is processed batch wise in the system of method of the invention. Each processed blood or processed blood component is optionally collected in a container. Said processed blood or component is also returned to the patient in cycles. Draw and return cycles are sequentially repeated during a selected period of time, whereby blood and/or blood components are cyclically removed from a subject, cyclically accumulated in the reservoir and cyclically returned to the patient.

A patient or subject is preferably a human.

The invention further provides methods for detecting the presence of pathogens in blood or blood products comprising RBCs, including disease causing infectious pathogens, methods for identifying such pathogens and methods for diagnosing infections in the blood of a patient and diagnosis of sepsis or a developing sepsis. Now that the present invention provides the insight that RBCs after binding complement opsonized pathogens alter their phenotype, it has become possible to use this characteristic of RBCs to capture such RBCs to a support comprising a non-specific RBC adhesion molecule binder according to the invention in a sample of blood or a blood product comprising RBCs and detect the presence of such pathogen-bound RBCs bound to the support, optionally followed by identification of the pathogen.

In one embodiment is therefore provided a method for detecting pathogens in a sample of blood or of a blood product comprising red blood cells (RBCs), the method comprising:
i) contacting said sample with a support comprising a non-specific RBC adhesion molecule binder to allow binding of RBCs that have bound at least one pathogen to said binder;
ii) detecting the presence of RBCs that have bound at least one pathogen.

Said method optionally comprises separating said sample into at least two components prior to step i), a first component comprising red blood cells (RBCs) and substantially free of white blood cells (WBCs) and platelets and a second component comprising WBCs and platelets and substantially free of RBCs, wherein step i) comprises contacting said first component of said sample with a support comprising a non-specific RBC adhesion molecule binder to allow binding of said RBCs that have bound at least one pathogen to said binder. Such separation step can be carried out as described herein before, e.g. by centrifugation, counterflow centrifugation elutriation, size filtration, affinity chromatography or a combination of these techniques.

Contacting said sample with a support comprising a non-specific RBC adhesion molecule binder is carried out for a period of time sufficient to allow binding of RBCs that have bound at least one pathogen to said binder, preferably for at least 1 min, such as 1 min, 5 min, 10 min, 20 min, 30 min, or 60 min. Detection of pathogens using a method according to the invention can be carried out after or without isolation or enrichment of pathogen-bound RBCs that are bound to said support. Said method for detecting pathogens may therefore further comprise isolating pathogen-bound RBCs that are bound to said support from said sample. Isolation of pathogen-bound RBCs is for instance advantageous in order to remove, potentially interfering human DNA and/or haem from the sample to be processed further. Isolating said RBCs preferably comprises removing cells and other components in said sample that have not bound to said binder. For isolation of RBCs that have bound at least one pathogen preferably beads, such as magnetic beads, or a filter comprising a non-specific RBC adhesion molecule binder are used. For instance if magnetic beads are used, following binding of RBCs bound by at least one pathogen to the beads, these complexes are isolated from the blood or blood product sample by pulling them to a magnet. The supernatant can subsequently be discarded, thereby obtaining isolated beads bound by RBCs that have bound at least one pathogen. Alternatively, if a filter is used, isolation of RBCs bound by at least one pathogen is carried out by removing cells and other components in the blood or blood product sample that have not bound to the non-specific RBC adhesion molecule binder, for instance by washing the filter with a washing buffer. Further provided is a method for isolating and/or enriching pathogens from a sample of blood or of a blood product comprising red blood cells (RBCs), the method comprising:
i) contacting said sample with a support comprising a non-specific RBC adhesion molecule binder to allow binding of RBCs that have bound at least one pathogen to said binder;
ii) isolating RBCs that are bound to said support from said sample, preferably by removing cells and other components in said sample that have not bound to said binder.

Detecting the presence of RBCs that have bound at least one pathogen can be performed using any methods known for detecting RBCs and pathogens in the art. Preferred methods include microscopy, including confocal microscopy and/or fluorescent microscopy, and cytometry, including the use of a haemocytometer and flow cytometry. In a preferred embodiment, detecting the presence of RBCs that have bound at least one pathogen is carried out by flow cytometry, such as fluorescent flow cytometry. Examples of suitable flow cytometers include Fluorescence activated cell sorting (FACS™) system (Becton Dickinson) and CytoFLEX (Beckman Coulter). Suitable methods for detecting RBCs and pathogens using flow cytometry are known to those skilled in the art.

If cytometry, preferably flow cytometry, more preferably fluorescent flow cytometry, is used for detection of RBCs that have bound at least one pathogen, the support that is contacted with a sample of blood or a blood product comprising RBCs preferably comprises beads. Such beads can be directly analysed by flow cytometry, without the need to isolate and/or elute pathogen-bound RBCs that are bound to the beads. Said beads either essentially consist of, or are coated with a non-specific RBC adhesion molecule binder according to the invention, preferably a polymer or mixture of two or more polymers. Preferably, said beads are coated with said non-specific RBC adhesion molecule binder.

For instance, pathogen-bound RBCs that are bound to the support, preferably beads, are detected by cell sorting for RBCs and labelling of pathogens. As used herein, the term "sorting" refers to a method by which RBCs of a sample are sorted based on their optical and/or volumetric properties, such as their shape or fluorescent labelling. Labelling of pathogens is preferably fluorescent labelling. For the detection of pathogens, without necessarily identifying the pathogen, general pathogen or general bacteria, virus, parasite, etc. label can used. Such general pathogen detection methods are generally known in the art. Preferred, but not limiting examples, are DNA labelling, polymerase chain reaction (PCR) using pathogen non-specific consensus primers, and, pan genera detection (PGD) labels, the latter preferably if the pathogens are bacteria. Because RBCs do not contain DNA, detection of DNA associated with RBCs indicates that the RBCs have bound at least one pathogen. Examples of suitable DNA dyes include, but are not limited to, Hoechst, 4',6-diamidino-2-phenylindole (DAPI) and cyanine dyes such as thiazole orange (TO), oxazole yellow (YO), dimeric forms YOYO and TOTO, BOXTO, BETO, dimethylindole red (DIR), acridine orange and hydroxystilbamidine. Bacterial and fungal nucleic acids can be amplified nonspecifically by PCR using consensus primers. For instance, fungal DNA can be detected by means of PCR by amplifying a region of the 18 ssu rRNA. Suitable methods for such detection are described in WO 97/07238, which is incorporated herein by reference. Bacterial DNA can for instance be detected using consensus primers which bind to the highly conserved 16 S or 23 S regions of the rRNA. Suitable methods for such detection are described in Anthony et al. J. Clin. Microbiol. 2000, pp. 781-788, which is incorporated herein by reference. In addition, general detection of bacteria can be based on the detection of lipopolysaccharide (LPS) for Gram-negative bacteria or lipoteichoic acid (LTA) for Gram-positive bacteria. LPS and LTA can be detected by the use of specific fluorescently labelled antibodies, for instance using Pan Genera Detection (PGD) assay. Further, Gram-type specific broad-range PCR using specially designed Gram-positive or Gram-negative primers can be used to detect bacteria, for instance as described in Klausegger et al. J. Clin. Microbiol. 1999, pp. 464-466, incorporated herein by reference.

A method for detecting pathogens according to the invention may further comprise determining at least one characteristic of said pathogens, if RBCs that have bound at least one pathogen are detected in said sample. Said characteristic is preferably selected from the group consisting of the type of pathogens, e.g. whether said pathogens are bacteria, viruses, fungi and/or parasites, gram-positivity or gram-negativity if said pathogens are bacteria, the identity of the pathogen, i.e. the bacterial, viral, fungal and/or parasitic species and drug and/or antibiotic resistance of the pathogens.

Drug and/or antibiotic resistance is for instance determined by detection of resistance markers, including, but not limited mecA, aacA, ermA and ermC, tetM, tetK, blaSHV and blaCTX-M and methicillin resistance genes. Suitable tests are the MAGICPLEX™ Sepsis Real-time Test (Seegene, Korea), which detects three drug resistance markers (mecA, vanA and vanB) and VYOO® (SIRS Lab, Germany) which uses PCR to detect, inter alia, 5 antibiotic resistance genes including mecA, vanA/B, and probes for the â-lactamase resistance genes blaSHV and blaCTX-M.

The type of pathogen is for instance detected using consensus primers as described herein, such as for fungi and bacteria. Gram-positive bacteria and Gram-negative bacteria are for instance detected using Gram-type specific primers or LPS- and LTA-specific antibodies, preferably fluorescently labelled antibodies, as described herein.

Preferably the identity of the pathogen is determined in order to identify the pathogen inducing or capable of inducing sepsis. If the identity of the pathogen is determined, pathogen-bound RBCs that are bound to a support comprising a non-specific RBC adhesion molecule binder according to the invention are preferably isolated from the sample. Isolation can be achieved as described herein, e.g. by isolation of magnetic beads using a magnet or washing away non-bound cells and other components of the sample. Optionally, pathogen-bound RBCs bound to a support, preferably a filter or beads, are lysed following isolation. Lysis of said RBCs is preferably carried out to obtain pathogens from the blood or blood product sample that were bound to RBCs in said sample. The pathogens can subsequently be analysed to determine at least one characteristic thereof, preferably for determining the identity of the pathogen. Methods and materials for lysis of RBCs are well known in the art. For example, RBCs are lysed by osmotic shock, such as by incubation with water, as described in the Experimental part herein, or by using a commercially available RBC lysis buffer, such as with a MolYsis kit (Molzym GmbH, Bremen, Germany). The resulting suspension comprising pathogens can for instance be plated onto a suitable culture medium or inoculated in a suitable culture medium to allow expansion of the pathogen. Alternatively, the resulting suspension is directly used for identification of the pathogens. As an alternative to lysis of RBCs, at least one characteristic of pathogens present in the sample, preferably the identity of the pathogens, is determined while the pathogen-bound RBCs are still bound to the support, preferably following isolation of the pathogen-bound RBC-support complexes. In this embodiment, said support preferably comprises beads, preferably beads coated with a non-specific RBC adhesion molecule binder according to the invention, whereby said binder preferably is a polymer. In yet another embodiment, pathogen-bound RBCs are eluted from the support, e.g. filter or beads, comprising the non-specific RBC adhesion molecule binder before the identity of the pathogen is determined.

Once pathogen-bound RBCs have been captured by a non-specific RBC adhesion molecule binder and isolated with a method according to the invention, the identity of the pathogens can be determined using any known methods available in the art. Suitable methods include detection of pathogen-specific nucleic acids, mass spectrometry, in situ hybridisation, including fluorescence in situ hybridisation (FISH), immunoassays and/or flow cytometric analysis.

For detection of pathogen-specific nucleic acids, nucleic acid, e.g. DNA or RNA, of the pathogen is isolated. Nucleic acid is for instance isolated directly following isolation of pathogen-bound RBCs from the sample of blood or blood product. Alternatively, nucleic acid is isolated following isolation of pathogen-bound RBCs from the sample of blood or blood product and subsequently lysis of RBCs, either directly from the resulting suspension or after culturing the pathogens in or on culture medium. Nucleic acid can be isolated using any standard nucleic acid isolation method known in the art. Identification of the pathogenic species is for instance carried out using pathogen-specific primers and/or probes. Suitable methods for instance include performing a polymerase chain reaction (PCR) followed by detection of amplified nucleic acid. Suitable primers and probes for detection of common sepsis-causing or infection-causing pathogens are widely and commercially available. Examples of multiplex PCR detection include MAGICPLEX™ Sepsis Real-time Test (Seegene, Korea), SEPTIFAST® (Roche Diagnostics Germany), SEPSITEST® (Molzym, Germany), VYOO® (SIRS Lab, Germany), The PROVE-IT™ Sepsis StripArray technology (Mobidiag, Finland). MAGICPLEX™ Sepsis Real-time Test screens for more than 90 pathogens which cover over 90% of sepsis-causing pathogens as well as 3 drug resistance markers (mecA, vanA and vanB) from whole blood sample. SEPTIFAST® detects 25 pathogens including gram-positive and gram-negative bacteria plus *Aspergillus fumigatus* and several species of *Candida*. SEPSITEST® can detect more than 345 bacteria and fungi and incorporates separate DNA extraction and purification of pathogen DNA with PCR and sequencing. VYOO® uses PCR to detect 33 bacteria, 7 fungi, and 5 antibiotic resistance genes including mecA, vanA/B, and probes for the â-lactamase resistance genes blaSHV and blaCTX-M in sepsis. The PROVE-IT™ Sepsis StripArray technology uses a combination of PCR and microarray to evaluate pathogens from incubated blood cultures. It can detect over 60 types of gram-negative and gram-positive bacteria. In addition, the methicillin resistance gene found in MRSA and many coagulase-negative staphylococci (CoNS) are also amplified and detected. These assays are reviewed in Lebovitz et al. (Molecular diagnosis & therapy. 2013; 17(4):221-231), which is incorporated herein by reference.

Identification of pathogens, including infection-causing pathogens and sepsis-causing pathogens, by mass spectrometry is based on protein profile characteristics of the pathogens. Using matrix-assisted laser-desorption/ionization time-of-flight mass spectrometry (MALDI-TOF MS) a broad spectrum of pathogens, including Gram-positive bacteria, Gram-negative bacteria, mycobacteria and fungi can be identified. A suitable method for sample preparation protocol (MALDI Sepsityper, Bruker Daltonic, Bremen, Germany) and analysis using a commercially available mass spectrometer (MALDI Biotyper, BrukerDaltonic) is described in Schubert et al. (J Mol Diagn 2011, 13:701-706), which is incorporated herein by reference. In brief, the method comprises, following capture of RBC-pathogens from blood or RBC fraction of blood using a method of the invention, wash unbound cells off using wash buffer SAGM; lyse blood cells using lysis buffer of MALDI Sepsityper (Bruker Daltonik, Bremen, Germany); collect pathogens (bacteria/yeast); wash using wash buffer; collect pathogens; concentrate by centrifugation and proceed according to extraction protocol described in Schubert et al. (2011) followed by mass spectrometry detection using commercially available mass spectrometry typing system (MALDI Biotyper; Bruker Daltonik) for the rapid and reliable identification of bacteria. Suitable other Mass spectrometer systems are commercially available, as is known to the person skilled in the art.

Alternatively, or additionally, mass spectrometry can be used following DNA amplification by for instance PCR to analyze the amplified nucleic acid in order to identify pathogens. A suitable method for PCR followed by electrospray ionization mass spectrometry (PCR/ESI-MS) which allows for the rapid and accurate identification of pathogens is described in Bacconi et al. (2014—Journal of Clinical Microbiology, 52(9): 3164-3174), which is incorporated herein by reference.

Methods for detecting pathogens and/or identifying said pathogens according to the invention are particularly suitable for rapid diagnosis of sepsis. The present inventors have further found that pathogens in blood can already be detected using the methods of the invention two days before a positive blood culture can be obtained. Hence, the methods of the invention allow for early detection of the presence of pathogens in the blood, for the early detection of sepsis, for prediction of the development of sepsis and for identification of sepsis-causing pathogens in blood. Therefore, a sample of blood or a blood product is preferably a sample from an individual suffering from sepsis, an individual suspected of suffering from sepsis, an individual at risk of suffering from sepsis or an individual suspected of having an infectious pathogen in the blood.

Further provided is a method for identifying pathogens, in a sample of blood or a blood product comprising red blood cells (RBCs), the method comprising:

i) contacting said sample with a support comprising a non-specific RBC adhesion molecule binder to allow binding of RBCs that have bound at least one pathogen to said binder;
ii) isolating RBCs that are bound to said support from said sample, preferably by removing cells and other components in said sample that have not bound to said binder; and
iii) identifying the pathogen that is bound to said RBCs bound to said support. Said pathogens are preferably infection-causing pathogens and/or sepsis-causing pathogens.

Also provided is a method for diagnosing an infection in the blood of a patient, the method comprising detecting pathogens and/or identifying pathogens in a sample of blood or a blood product comprising red blood cells (RBCs) of said patient with a method according to the invention. The identity of pathogens can be determined using any method known in the art and any of the methods described herein, including detection of pathogen-specific nucleic acids using primers and/or probes, mass spectrometry of pathogen proteins or amplified nucleic acids, flow cytometry using pathogen-specific labels and in-situ hybridisation using pathogen-specific probes. Such method is in one embodiment for diagnosing sepsis or a developing sepsis in the patient. In another embodiment, such method is a method for diagnosing an infection present in the blood of the patient. In one embodiment, said pathogens are sepsis-causing pathogens. If pathogens bound to RBCs are detected in the sample, the patient from which the sample is derived is suffering from an infection in the blood and/or the patient may be suffering from sepsis or sepsis may be developing in said patient. Hence, the method preferably further comprises determining that an infectious pathogen is present in the blood of said patient if pathogens are detected in said sample and/or the identity of the pathogen is determined. In that case, the patient is suffering from an infection in the blood and/or suffering from sepsis and/or sepsis may be developing in said patient.

In addition, methods for detecting pathogens and/or identifying said pathogens according to the invention are suitable for rapid detection of antibiotic susceptibility of said pathogens. Provided is therefore a method for determining susceptibility for antibiotics of a pathogen, the method comprising, detecting pathogens and/or identifying pathogens in a sample of blood or a blood product comprising red blood cells (RBCs) with a method according to the invention;

isolating RBCs that are bound to said support from said sample;

contacting said isolated RBCs that are bound to said support with one or more antibiotic agents; and determining growth and/or a functional activity of the pathogen.

Growth and/or a functional activity of the pathogen is preferably determined following incubation of the pathogen in or on a culture medium. Hence, said method preferably further comprises incubating the pathogen in or on a culture medium. Preferably, the pathogen is isolated from the RBC before such incubation, preferably by lysis of the RBCs. Growth and/or a functional activity of the pathogen is preferably determined as compared to a reference comprising pathogen-bound RBCs, preferably pathogen-bound RBCs obtained from the same sample of blood or a blood product, that are captured by a support comprising a non-specific RBC adhesion molecule binder according to the invention, and subsequently isolated, and optionally, incubated in or on the same culture medium, but that have not been contacted with said one or more antibiotic agents. Contacting said isolated RBCs that are bound to said support with one or more antibiotic agents is carried out for a period of time sufficient to allow said one or more antibiotic agents to interact with the pathogen, preferably for at least 1 min, such as 1 min, 5 min, 10 min, 20 min, 30 min, or 60 min. If the growth and/or a functional activity of the pathogen that has been contacted with said one or more antibiotic agent is less than the growth and/or a functional activity of the pathogen that has not been contacted with said one or more antibiotic agents, said pathogen is susceptible to said one or more antibiotic agents. Examples of functional activity of a pathogen that can be determined when carrying out a method of the invention include metabolic activity and viability. For instance resazurin, carboxyfluorescein succidimyl ester, tetrazolium compounds protease markers, and/or ATP can be detected as a measure for metabolic activity. Once it has been determined that a pathogen is susceptible to a specific antibiotic agent, the patient suffering from an infection or sepsis induced by said pathogen is preferably treated with the antibiotic agent.

As demonstrated in the Experimental part herein, is was further found that the number of RBCs in blood that are bound by pathogens and adopt a "sticky" phenotype is unexpectedly high. This percentage can be as high as between 1% and 2% of the total RBCs in blood. Due to this high percentage of pathogen-bound RBCs, such cells were already observable two days before a positive blood culture can be obtained. Such high percentage allows the detection of pathogens in blood at a early stage, before sepsis is present or diagnosed by other methods, including blood culture (especially if antibiotic treatment was started prior obtaining a sample for blood culture), by analysing a blood sample for the presence of RBCs that have bound at least one pathogen. In addition, the high percentage of positive RBCs, i.e. RBCs that are bound by pathogens, allows the detection thereof in a small sample of whole blood. Further provided is therefore a method for determining the presence of pathogens in a whole blood sample of an individual having an infectious pathogen in the blood, suspected of having an infectious pathogen in the blood, suffering from sepsis, suspected of suffering from sepsis or at risk of developing sepsis, the method comprising detecting the presence of red blood cells (RBCs) that have bound at least one pathogen using cytometry or microscopy. Preferably said individual is suspected of having an infectious pathogen in the blood, suspected of suffering from sepsis or at risk of developing sepsis. Suitable techniques include the use of a hemacytometer, flow cytometry, confocal microscopy and fluorescence microscopy.

In one embodiment, said detecting step is carried out by flow cytometry as this allows for a very rapid detection of pathogens. Preferably RBCs that have bound at least one pathogen are detected by cell sorting for RBCs and labelling of pathogens, as described herein. In a preferred embodiment, said labelling of pathogens comprises DNA labelling. In another preferred embodiment, said method comprises determining the presence of bacteria and said labelling comprises labelling with a general bacteria label. As described herein before, general bacteria labels include LPS-specific antibodies for detection of gram-negative bacteria and/or LTA-specific antibodies for detection of gram-positive bacteria.

Once it has been established that pathogens are present in a sample of blood or blood product, a patient is preferably treated in accordance with the invention. Preferably, pathogens are removed from blood of said patient using a method described herein. Provided is therefore a method for the removal of a pathogen from blood of a patient in need thereof comprising:

determining the presence of pathogens in a whole blood sample of an individual having an infectious pathogen in the blood, suspected of having an infectious pathogen in the blood, suffering from sepsis, suspected of suffering from sepsis or at risk of developing sepsis with a method according to the invention;

withdrawing blood from said patient;

separating said blood into at least two blood components, a first component comprising red blood cells (RBCs) and substantially free of white blood cells (WBCs) and platelets and a second component comprising WBCs and platelets and substantially free of RBCs;

contacting said first component with a support, preferably a filter, comprising a non-specific RBC adhesion molecule binder thereby depleting said first component of RBCs that have bound at least one pathogen;

optionally combining said first component that is depleted of RBCs that have bound at least one pathogen and said second component;

returning said first component that is depleted of RBCs that have bound at least one pathogen and said second component to said patient.

A system for removing a pathogen from blood or a blood product in accordance with the present invention is particularly suitable for the substantial removal of a pathogen from blood or a blood product. For example, the system can be used to remove a pathogen from blood or a blood product in order to provide blood or a blood product substantially free of pathogens, or at least substantially free of pathogens bound to red blood cells (RBCs).

Preferably, the system is arranged to be used for depleting blood of a patient, e.g. a patient suffering from sepsis or an infection in the blood, substantially of pathogens, or at least substantially of pathogens bound to red blood cells (RBCs).

Alternatively or additionally, the system may be arranged to be used to deplete blood or a blood product, e.g. donor blood or a donor blood product and/or blood or a blood product contained in a container such as a blood bag, substantially of pathogens, or at least substantially free of pathogens bound to red blood cells (RBCs). It is noted that the system may be used in vitro.

Additionally or alternatively, the system may be arranged to be used for isolating pathogens, or at least pathogens bound to red blood cells (RBCs), from blood or a blood product. This may for instance be advantageous if the pathogens need to be studied, for instance in order to determine the type and species of the pathogens.

The system may also be used differently, for example in order to train people, such as medical staff, such as for instance in an in vitro setting.

A system provided by the invention comprises:

a separation device, for separating said blood or said blood product into at least a first component comprising RBCs and being substantially free of WBCs and platelets and a second component comprising WBCs and platelets and being substantially free of RBCs; and a filter device for depleting said first component substantially of RBCs that have bound at least one pathogen, said filter device comprising a non-specific RBC adhesion molecule binder. Said separation device preferably comprises a centrifuge. Said non-specific RBC adhesion molecule binder is preferably a polymer.

Said system can be used, by means of said separation device, to separate WBCs and platelets from RBCs substantially, before subsequently substantially filtering, by means of said filter device, the RBCs that have bound at least one pathogen out of a component comprising RBCs, of which component a portion has preferably bound at least one pathogen, which portion is then substantially free of WBCs and platelets. Hence, the filter device can substantially filter out pathogen bound RBCs without unintentionally filtering out a large number of WBCs and platelets at the same moment. This can be an advantage for various reasons. For example, the system can provide a relatively easy and/or reliable system for substantially removing any pathogen bound to a RBC, or at least substantially removing different pathogens bound to RBCs, from a blood or blood product, without the need of having a specific filter device for the specific pathogens bound to RBCs present in the blood or blood product. Actually, the system of the present invention may therefore for instance be used to substantially remove the RBC bound pathogens without needing to know what specific pathogens or RBC bound pathogens are present in the blood or blood product. Moreover, due to the arrangement of the system, it can be prevented that the filter device of the system unintentionally filters most WBCs and platelets together with the RBC bound pathogens from the blood or blood product. It is noted that not substantially filtering the WBCs and platelets away together with the RBC bound pathogens may not only facilitate that the filter device can be used for a relatively long period of time without maintenance, as the filter device will less soon become obstructed by filtered out particles as substantially no WBCs and platelets are fed through the filter device, but may also facilitate that a cleaned end product, e.g. cleaned blood or a cleaned blood product, can be provided which includes WBCs and platelets, e.g. includes almost or substantially all the WBCs and platelets and preferably substantially all RBCs that have not bound a pathogen that were present in the initial blood or blood product then still to be cleaned. Preferably, the system can thereto be arranged to reunite the first and the second component after the first component of the blood or blood product has been depleted of pathogen bound RBCs by its filter device.

Further provided is a pathogen bound RBC filter device for use in a system according to the invention, wherein said pathogen bound RBC filter device is arranged for depleting a blood product substantially of RBCs that have bound at least one pathogen, said filter device comprising a non-specific RBC adhesion molecule binder. Said non-specific RBC adhesion molecule binder is preferably a polymer, more preferably a polymer selected from a group consisting of polyester, polyurethane, cellulose, nylon, nitrocellulose, polypropylene, polyethylene terephthalate, polyimide, polyvinyl alcohol, and polyvinylidene fluoride. Preferably said pathogen bound RBC filter device is arranged for depleting a blood component comprising RBCs that is substantially free of WBCs and platelets of RBCs that have bound at least one pathogen.

Advantageous embodiments according to the invention are described in the appended claims.

By way of non-limiting examples only, embodiments of the present invention will now be described with reference to the accompanying figures in which:

It is noted that the figures, especially FIGS. 6-9, show merely preferred embodiments according to the invention. In the figures, the same or similar reference signs or numbers refer to equal or corresponding parts.

Figure 1:
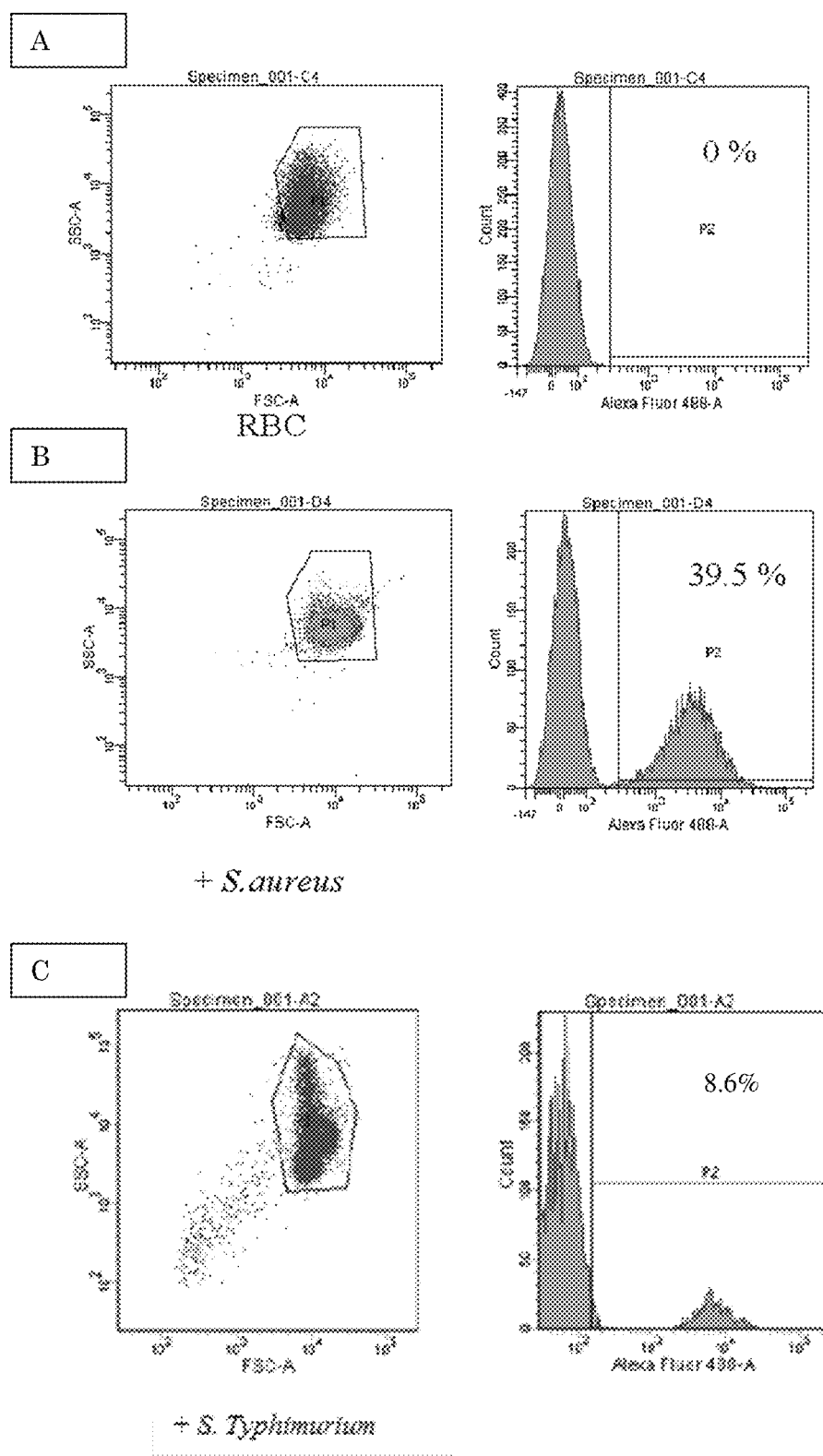
FIGS. 1A-1F show schematic plots of bacterial binding to RBCs.
Figure 1:
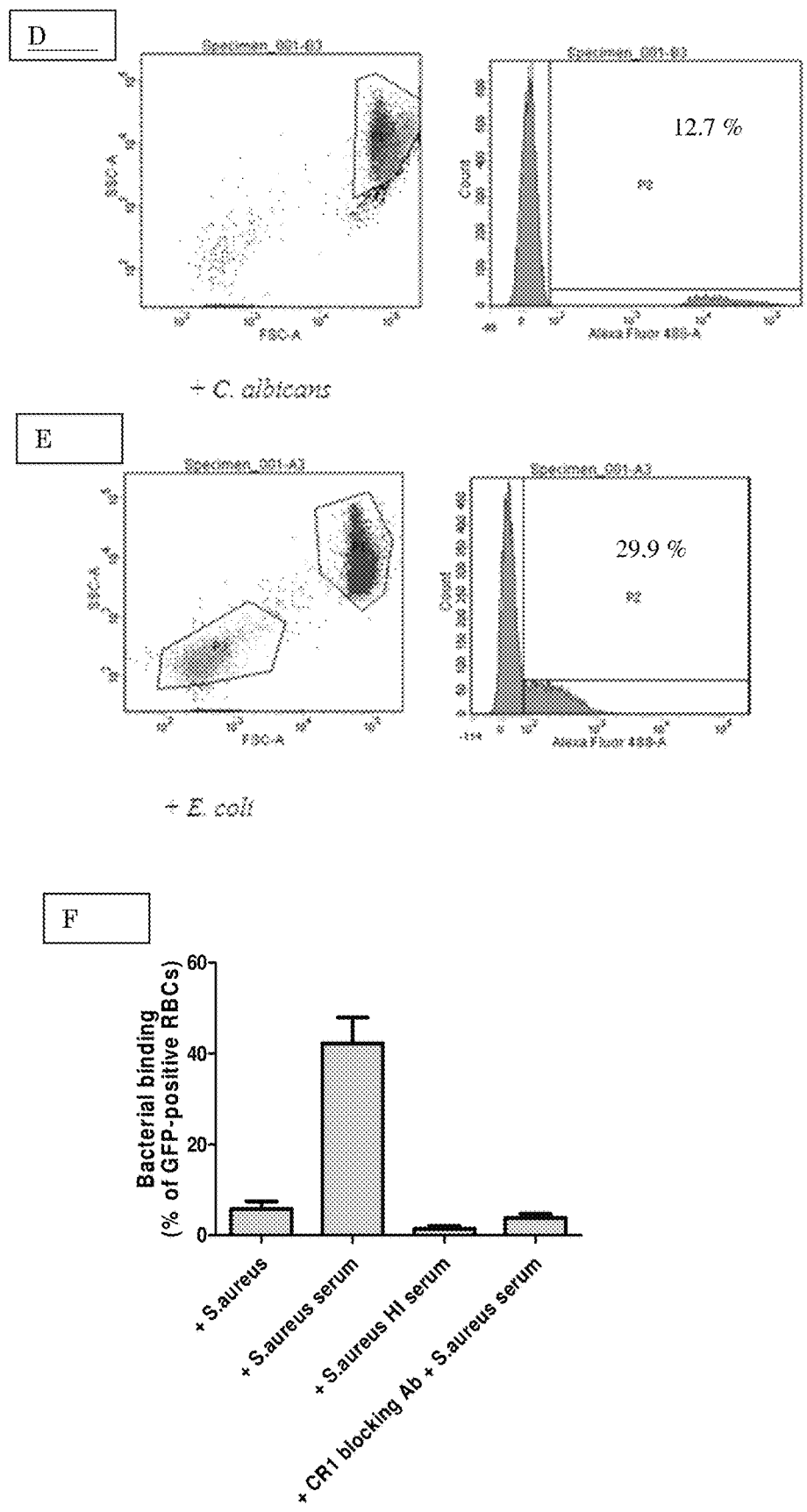

FIG. 1 shows that microbial binding is dependent on complement and CR1. FIGS. 1A-1E: flow cytometric analysis of microbe binding to RBCs. After incubation with a serum-treated microbe, RBCs were analysed by flow cytometry. FIG. 1A-E represent dot-plots of RBCs (PI). P2 shows the % of RBCs that have bound opsonized $S.$ $aureus$ (B), $S.$ $typhimurium$ (C), $C.$ $albicans$ (D) or $E.$ $coli$ (E). FIG. 1F: microbial binding to RBCs is strongly enhanced by opsonisation and is dependent on complement. Prior to incubation with RBCs, a fraction of $S.$ $aureus$ was treated with 50% human AB pool serum for 30 min at 37° C. Next, a binding experiment was performed. RBCs were analysed by flow cytometry. Bacterial binding was measured as % of GFP-positive RBCs. In case $S.$ $aureus$ was treated with serum, a high increase in binding to RBCs was observed in comparison with non-opsonized bacteria. Moreover, a very low binding was detected when bacteria were pre-incubated with heat-inactivated (HI) serum. Bacterial binding was completely abolished when RBCs were pre-incubated with CR1 blocking antibody. These findings show that complement found in serum and CR1 on RBCs are necessary to ensure bacterial binding to RBCs. n=7+/−SEM.

Figure 2:
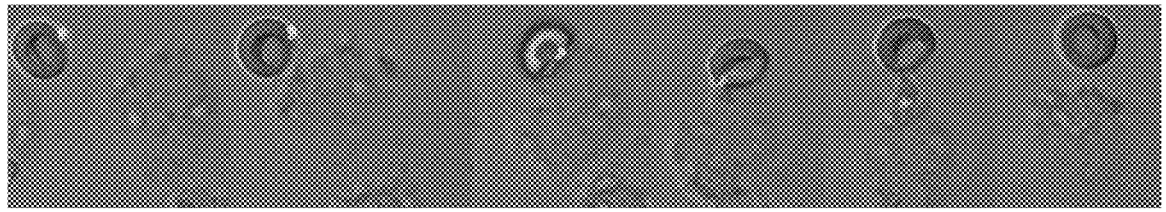
FIG. 2 shows images of a RBC carrying a bacterium on its membrane and transferring this to a monocyte under static conditions.

FIG. 2 shows the transfer of $S.$ $aureus$ to monocytes. Live imaging of GFP-expressing $S.$ $aureus$ bound to RBCs added to freshly isolated human monocytes reveals bacterial transfer from the erythrocyte to the phagocyte under static conditions. Images 1-3 of FIG. 2 show RBC carrying a bacterium on its membrane in close proximity to a monocyte. In images 4-5 of FIG. 2, bacterial transfer is seen. Image 6 of FIG. 2 shows that the bacterium is lost from the RBC and delivered to the monocyte.

Figure 3:
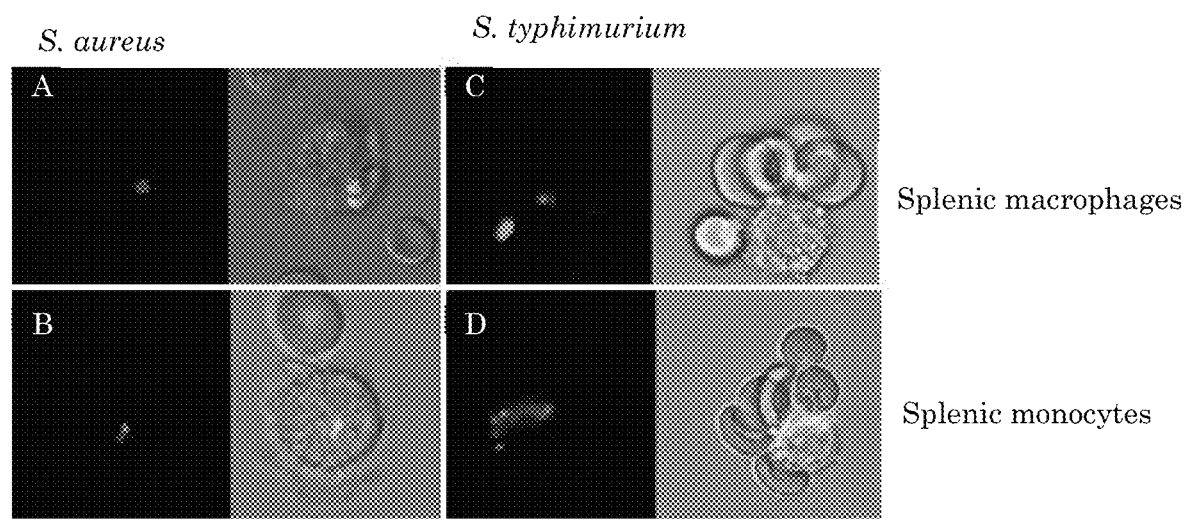
FIG. 3 shows images of transfer of bacteria to splenic monocytes and macrophages under flow.

FIG. 3 shows transfer of $S.$ $aureus$ and $S.$ $typhimurium$ to splenic monocytes and macrophages. Monocytes (CD163+) and macrophages (CD163+ and auto fluorescent) are selected to perform live imaging of bacterial transfer using GFP-expressing $S.$ $aureus$ (FIG. 3A-B) or $S.$ $typhimurium$ (C-D) bound to RBCs under flow conditions. Bacterial transfer to the phagocytes of the RES is shown.

Figure 4:
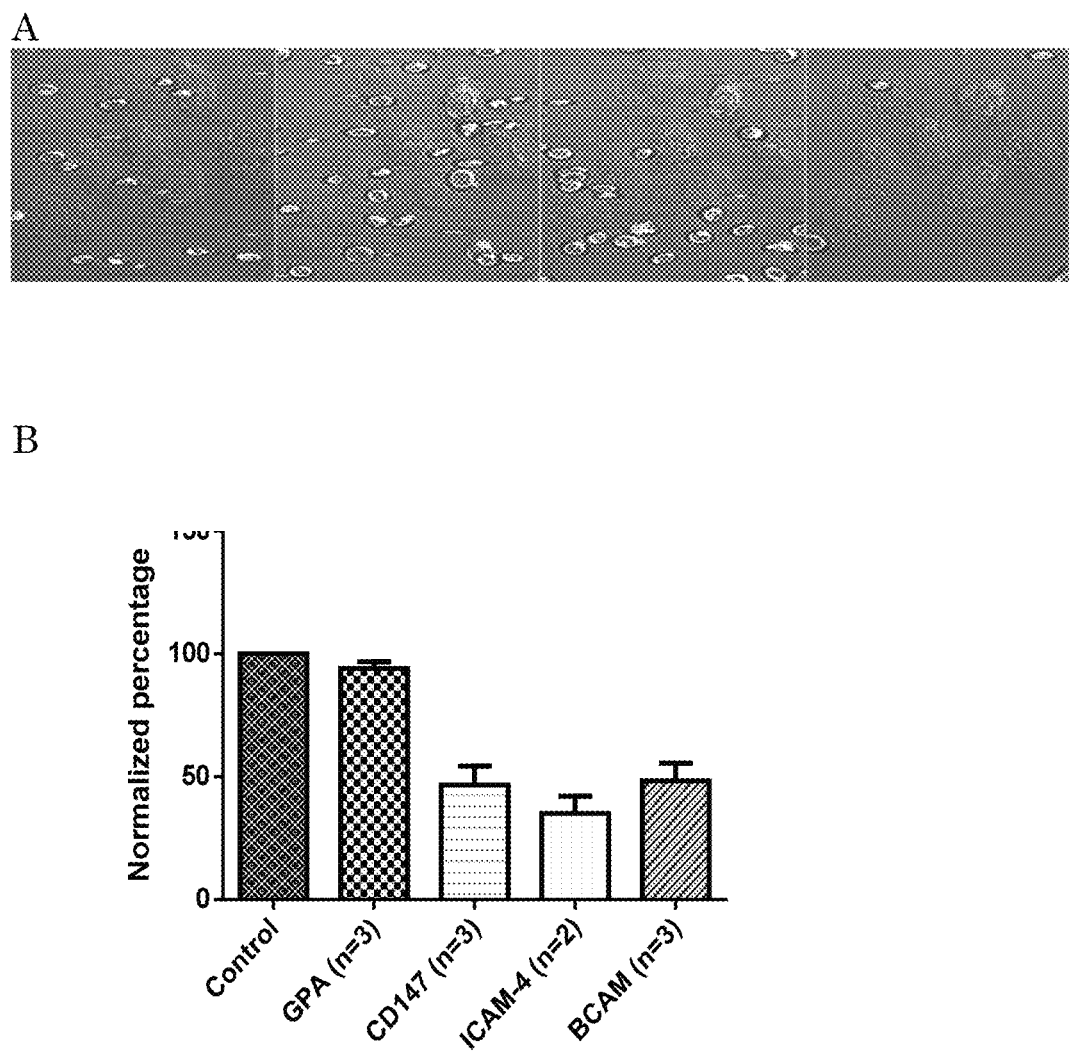
FIG. 4 shows a bacterial transfer from RBCs to monocytes under flow and the importance of RBC adhesion molecules in this process.

FIG. 4 shows blocking adhesion molecules on RBCs inhibits bacterial transfer. Monocytes were isolated from whole blood and seeded on a 0.4 uM Ibidi flow chamber. RBCs with bound $S.$ $aureus$ on their surface were further treated with Lu/BCAM, CD147 or ICAM-4 blocking antibody. Next the RBCs were flown over the monocytes at the speed of 4.5 ml/hr (0.2 dyn) and tracked in time. The aforementioned antibodies used induced a significant reduction of bacterial transfer. When combined, no additional reduction was seen. Glycophorine A (GPA) blocking antibody was used as a control, showing that a reduction in bacterial transfer is not induced when using a random antibody against an abundant antigen on the RBC membrane.

Figure 5:
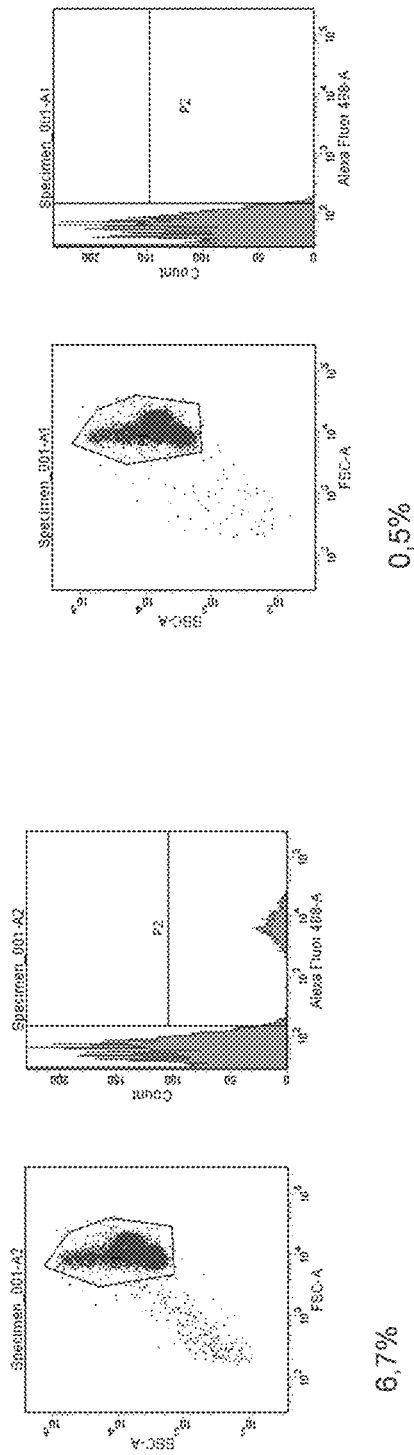
FIG. 5 shows capturing of RBCs carrying bacteria by a non-specific RBC adhesion molecule binder (a leukocyte reduction filter)
Figure 5:
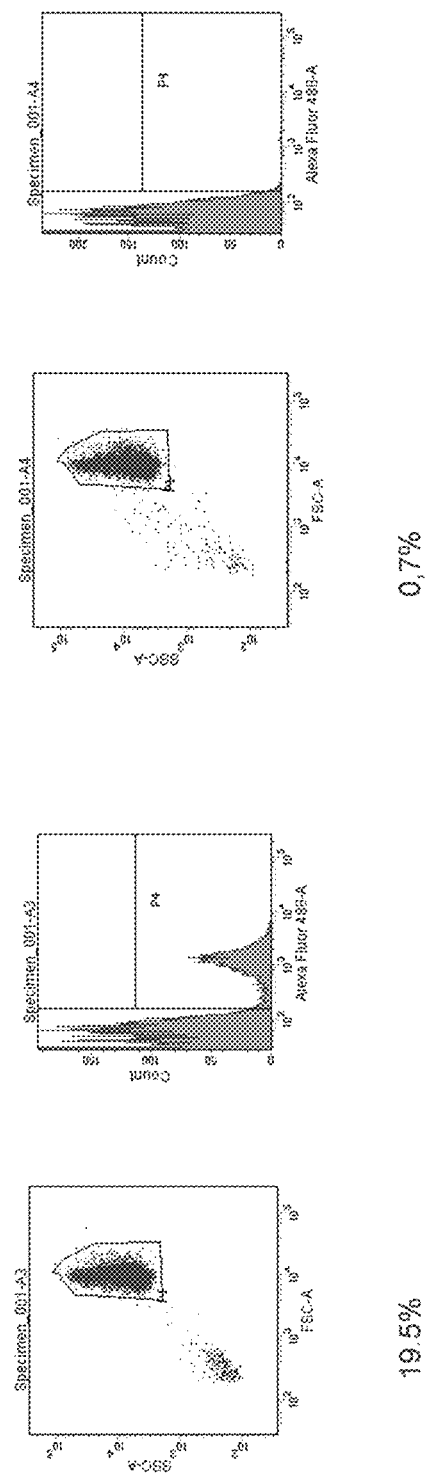

FIG. 5 shows RBC carrying opsonized *S. aureus* can be captured from blood by a non-specific RBC adhesion molecule binder. FIG. 5A: a RBC suspension containing *C. albicans* carrying RBC was flown over a leukocyte reduction filter. Shown here, are the FACS plots of the RBC suspension before and after filtration. FIG. 5B: a RBC suspension containing *S. aureus* carrying RBC which was flown over a leukocyte reduction filter. Shown here are the FACS plots of the RBC suspension before and after filtration.

Figure 10:
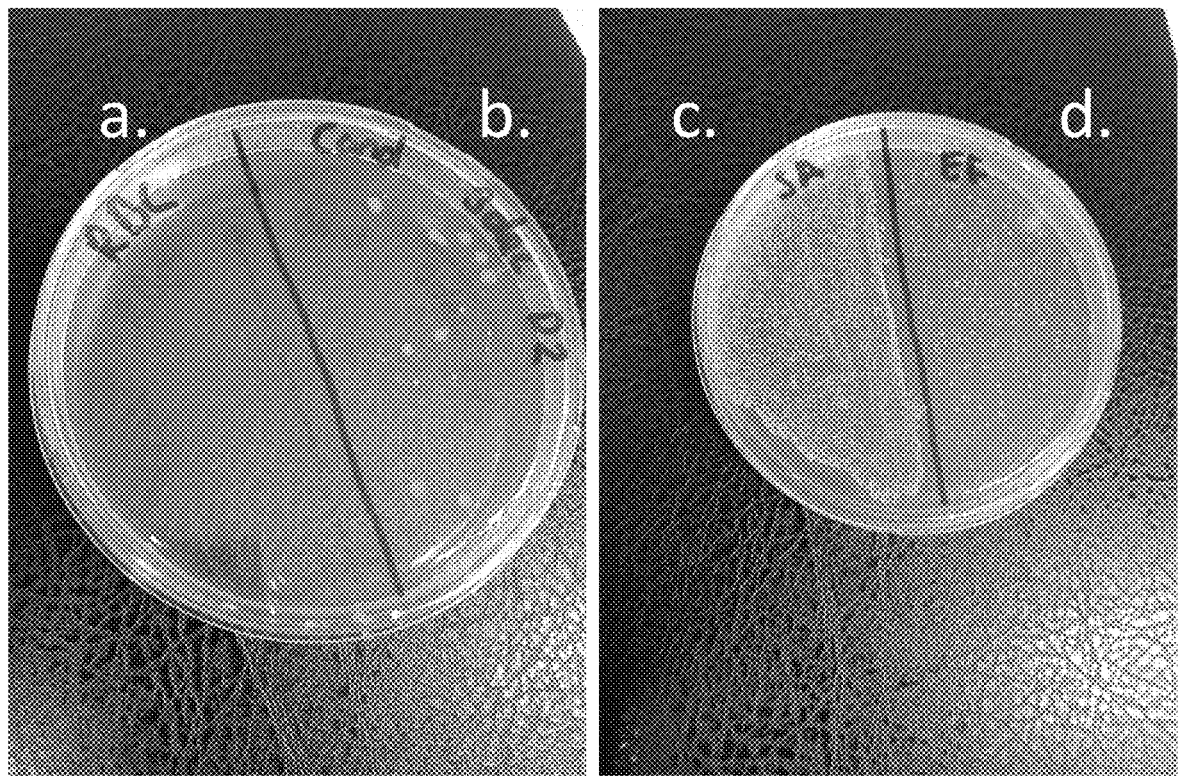
FIG. 10 shows plating of isolated microorganisms after lysis of RBC-pathogen complexes.

FIG. 10 shows plating of isolated microorganisms after lysis of RBC-pathogen complexes. In a the fraction of a control RBC suspension is plated, in b, c, and d the fractions of *C. albicans, S. aureus* and *E. feacalis* are plated, respectively.

Figure 11:
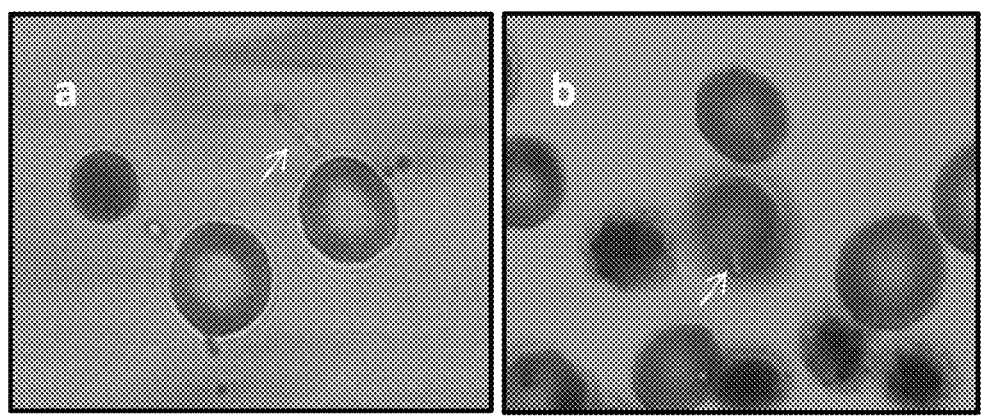
FIG. 11 shows microscopic images of patient samples.

FIG. 11 shows microscopic images of patient samples. FIG. 10A: Sample of a patient suffering from *K. pneumoniae* induced sepsis, arrow indicates *K. pneumoniae* bound by a RBC; FIG. 10B: Sample of a patient suffering from *E. coli* induced sepsis, arrow indicates *E. coli* bound by a RBC, stained by Hoechst DNA dye.

Figure 12:
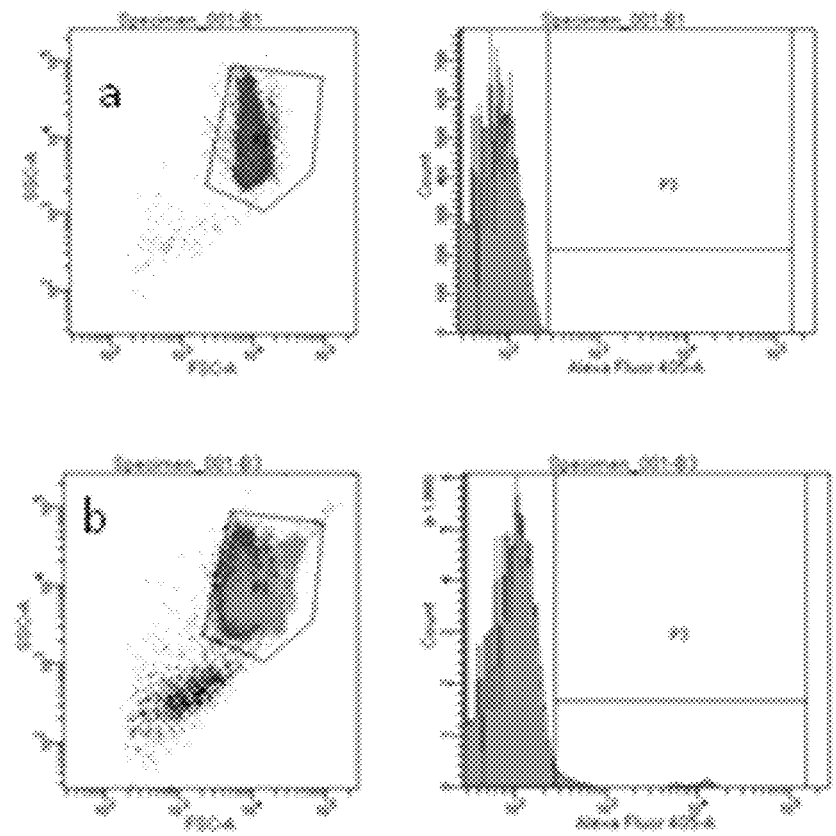
FIG. 12 shows flow cytometric analysis of RBCs from patient samples stained with Hoechst DNA dye.

FIG. 12 shows flow cytometric analysis of RBCs from patient samples stained with Hoechst DNA dye. FIG. 11A Red blood cell sample of a healthy control, showing no DNA staining; FIG. 11B: Red blood cell sample of the septic patient depicted in FIG. 10B, showing DNA positive RBC (RBC gated on FSC and SSC; positive signal in 405 channel), indicative for RBC-pathogen complexes.

FIGS. 6-9 show schematic views of different embodiments of a system 1 according to an aspect of the invention. Said system 1 is a system 1 for removing a pathogen from blood or a blood product, preferably from blood of patient in need of such removal. The system 1 comprises a separation device 2 for separating said blood or said blood product into at least a first component comprising RBCs and being substantially free of WBCs and platelets and a second component comprising WBCs and platelets and being substantially free of RBCs.

In embodiments, the separation device 2, which can be or include an apheresis unit for depleting said blood or said blood product substantially of WBCs and platelets, can for instance be or comprise a centrifuge. However, the separation device 2 can comprise or be formed by any other separation device suitable for separating the WBCs and platelets from the RBCs. An alternative separation device may be formed e.g. by a counterflow device, a centrifugation elutriation device, a size filtration device, for instance comprising one or more membranes or so-called sieve membranes, an affinity chromatography device, and/or a device combining two or more of the techniques utilized by the fore-mentioned devices. Said separation device preferably comprises a centrifuge. It is noted that said separation device 2, e.g. said centrifuge, may comprise at least two compartments to keep the separated components separated. For example, the components can be stored temporarily in the respective compartments and/or the respective components can be taken from the separation device 2 by removing them from said compartments.

The system 1 further comprises a filter device 3 for depleting said first component of RBCs that have bound at least one pathogen. Said filter device 3 comprises a non-specific RBC adhesion molecule binder.

Preferably, said non-specific RBC adhesion molecule binder is a polymer, more preferably a polymer selected from a group consisting of polyester, polyurethane, cellulose, nylon, nitrocellulose, polypropylene, polyethylene terephthalate, polyimide, polyvinyl alcohol, and polyvinylidene fluoride.

It is noted that the system 1 can preferably be a closed sterile system. Although said system 1 can comprise individual elements or devices 2, 3, said system 1 or a part thereof can preferably be formed as an apparatus comprising at least some of the elements or devices 2, 3 of the system 1. For example, at least some, preferably all devices, of the system can be integrated into an apparatus for removing a pathogen from blood or a blood product. For example, such apparatus may comprise a frame and/or a housing 15 on and/or in which at least some of the elements or devices of the system 1 are situated. For example, an apparatus can comprise a housing 15 accommodating at least the separation device 2 and the filter device 3.

Advantageously, the system 1 can further comprise a conduit 4 for conducting said first component from the separation device 2, e.g. from a first outlet 2*b* thereof, to the filter device 3, e.g. to an inlet 3*a* thereof. For example, said first component can be conducted directly from the separation device 2 to the filter device 3. However, the system 1 may alternatively or additionally be arranged to store at least a part of the first component temporarily before it is fed to the filter device 3. In embodiments, a first component storage container may thereto be provided downstream the separation device 2 and upstream of the filter device 3.

Figure 9:
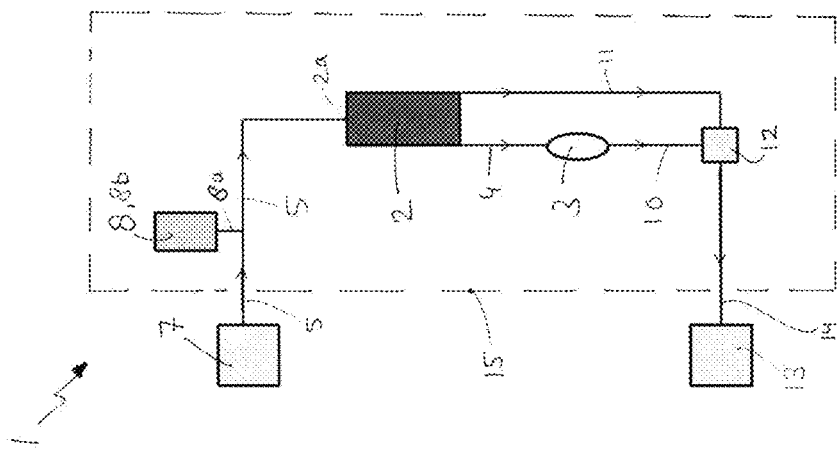
FIG. 9 shows a schematic view of a fourth embodiment of a system according to an aspect of the invention.

Further, as for instance can be seen in the exemplary embodiment of FIG. 9, the separation device 2 can have an inlet 2*a* for letting the blood or the blood product into the separation device 2, which inlet 2*a* may be connected to a blood or blood product supply conduit 5 for supplying the blood or blood product to the separation device 2, e.g. from container 7 or from a subject 9.

Figure 7:
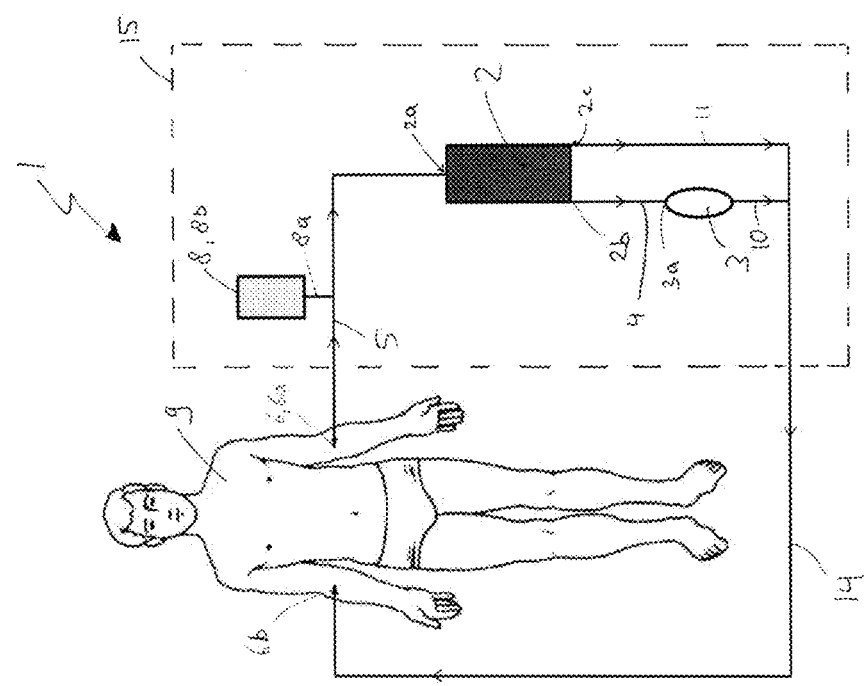
FIG. 7 shows a schematic view of a second embodiment of a system according to an aspect of the invention.
Figure 6:
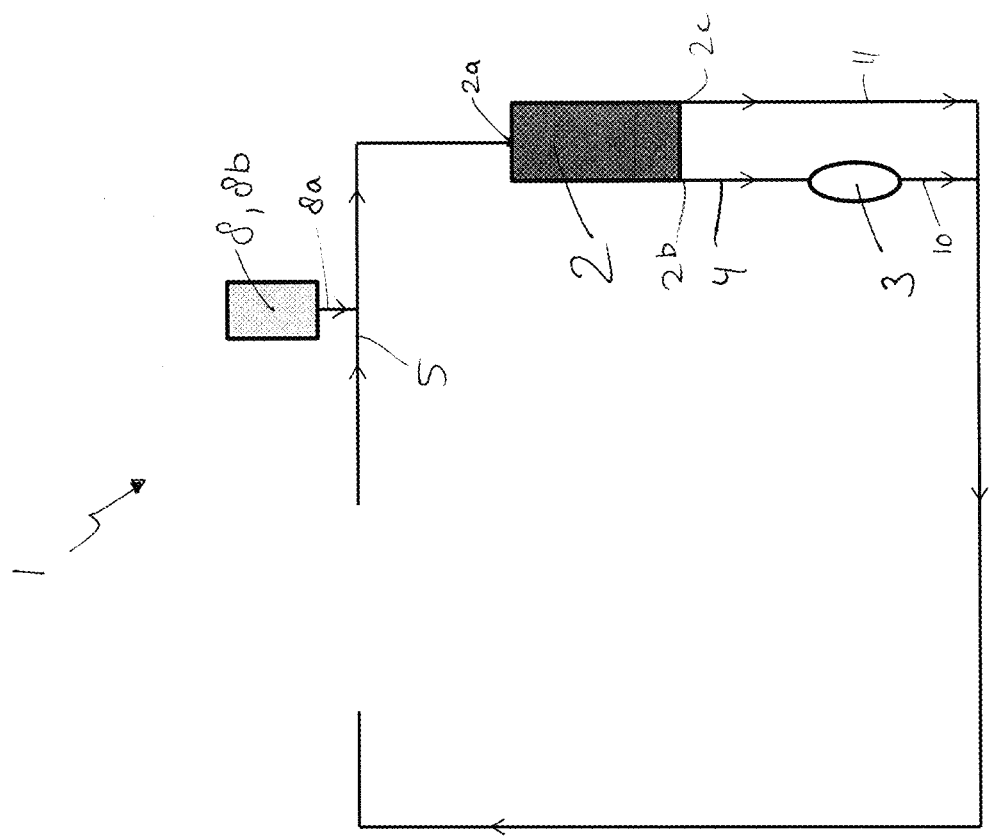
FIG. 6 shows a schematic view of a first embodiment of a system according to an aspect of the invention.
Figure 8:
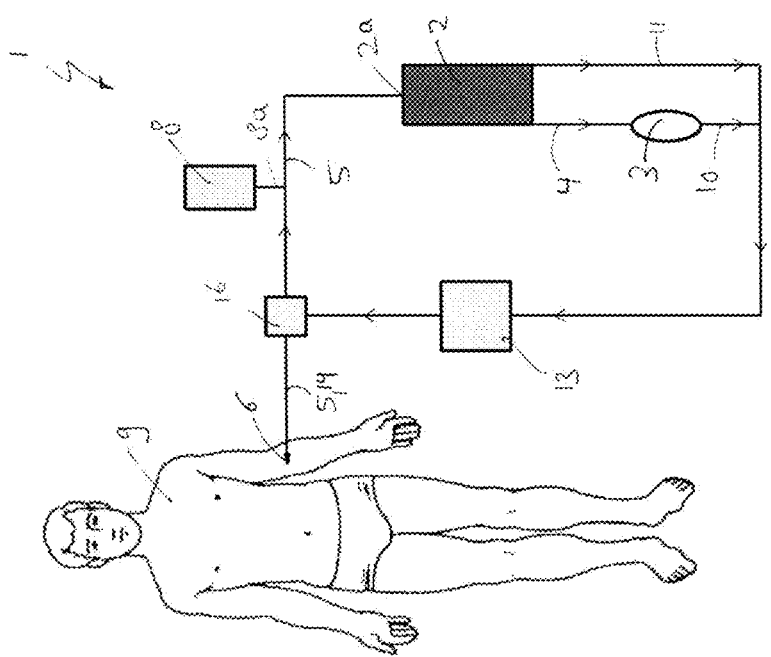
FIG. 8 shows a schematic view of a third embodiment of a system according to an aspect of the invention.

In embodiments, such as for instance in the embodiment of FIGS. 7 and 8, the system 1 may be arranged to conduct blood from a subject 9, such as for instance a patient, to the separation device 2. For example, the supply conduit 5 can therefore be provided with a blood collecting device, e.g. being or comprising a needle 6, such as for example a conventional apheresis needle. Hence, the separation device 2 may be arranged to be brought in fluid connection with a subjects bloodstream.

Alternatively or additionally, as for instance shown in FIG. 9, the system 1 may comprise, and/or may be arranged to be connected to, an initial blood or blood product container 7 for holding initial blood or an initial blood product from which RBC that have bound pathogens are to be removed. Said container 7 can for instance be filled with donor blood or with a blood sample or blood product sample which is to be filtered, for instance in order to remove pathogens, or at least RBC that have bound pathogens, and/or in order to obtain a substantially pathogen free blood or blood product and/or to obtain filtered out RBC that have bound pathogens, e.g. in order to enable executing tests on said pathogens.

It is noted that the system 1 may comprise an anticoagulant supply unit 8 for adding an anticoagulant to the blood or the blood product. Said anticoagulant supply unit 8 can preferably be situated upstream of the separation device, and more preferably can be arranged for feeding the anticoagulant, especially in a dosed and/or controlled manner, into a supply conduit 5 for supplying the blood or blood product to the separation device. Optionally, the anticoagulant supply unit 8 can comprise an anticoagulant supply conduit 8a, e.g. for feeding the anticoagulant to said blood or blood product supply conduit 5. It is noted that the system 1, e.g. its anticoagulant supply unit 8 and/or its anticoagulant supply conduit 8a, may comprise a dosing unit for dosing the anticoagulant. For example, the anticoagulant can be stored in an anticoagulant reservoir 8b, which can be part of said supply unit 8, and can be fed from said reservoir, via an anticoagulant supply conduit 8a, to the blood or blood product. Additionally or alternatively, the anticoagulant supply unit 8 may comprise an anticoagulant pump for pumping said anticoagulant to the blood or blood product.

Further, the system 1 may comprise a mixing chamber or other mixing means for mixing the anticoagulant with the blood of blood product.

It is noted that the separation device 2 of the system 1 may have a first outlet 2b for letting the first component, which is separated from the second component, out of the separation device 2. Preferably, said first outlet 2b can be in fluid connection with said filter device, e.g. it can be connected to an inlet of the filter device 3 by means of a conduit 4 for conducting said first component from the separation device 2 to the filter device 3.

Furthermore, it is noted that the system 1 may for example be arranged such that the system 1 can feed the filtered first component from the filter device 3 to a storage container 13. Alternatively or additionally, the system 1 may be arranged to feed the filtered first component directly to a subject 9 and/or to an administering device 6b for administering at least said filtered first component to a subject 9, preferably the subject from which the initial blood or blood product was taken. However, the blood or blood product substantially freed of pathogens may also be administered to another subject, e.g. after storing it temporarily.

Additionally or alternatively, the separation device 2 may have a second outlet 2c for letting the second component out of the separation device 2. In embodiments, said second outlet 2c can be in fluid connection with a second component outlet conduit 11, e.g. for conducting the separated second component away from the separation device 2. Although the second component comprising WBCs and platelets may in embodiments be stored, e.g. in a container for storing the second component, and/or administered without being combined with the filtered first component, or may even be disposed, the second component can advantageously be put together with the filtered first component, e.g. before storing them together and/or before administering them together to a subject. Preferably, said filtered first component and said second component can be put together, and preferably can be mixed, in a ratio corresponding to the ratio of the first component and second component initially present in the initial blood or blood product. It may be apparent that further, in case the initial blood or blood product was separated in more then two components, one or more, for instance all, of such further components can be put together with the filtered first component and the second component as well.

In advantageous embodiments, an outlet of the filter device 3 can be connected to an outlet conduit 10 for conducting the filtered first component, which is depleted of RBCs that have bound at least one pathogen, away from said filter device 3, e.g. in order to store it, to administer it and/or to put it together with at least the second component.

Preferably, the system 1 can be arranged to put the filtered first component and the second component of the blood or blood product together in order to obtain a blood or blood product substantially free of pathogens, or at least substantially free of RBC bound pathogens. For instance, as can be seen in the exemplary embodiments of FIGS. 6-9, the outlet conduit 10 for conducting the filtered first component away from the filter device 3 can merge with the second component outlet conduit at a certain point, such that the filtered first component and the second component can join, and preferably mix. In embodiments, such as for example the embodiment of FIG. 9, the system 1 may further comprise a mixing chamber or another mixing unit 12 for mixing said second component with said filtered first component to obtain a blood or blood product comprising RBCs and WBCs and platelets and being substantially free of RBC bound pathogens. Subsequently, said blood or blood product can be stored, e.g. in a container 13, for instance such as shown in the embodiment of FIG. 9. Alternatively, said blood or blood product can be fed, e.g. substantially directly, to a subject 9, e.g. by means of a supply conduit 14, which may be connected to an administering device 6b, such as an administering needle 6b. Hence, the first component that is depleted of RBCs that have bound at least one pathogen, combined with the second component can be fed to a subject, preferably returned to the subject from which the initial blood was taken.

Although the system 1, as for instance can be seen in the exemplary embodiment of FIG. 7, may for instance be arranged for continuous treatment and/or can preferably comprise a dual needle 6a, 6b configuration, the system 1 may alternatively, or additionally, be arranged for performing a cyclical treatment.

In the embodiment of FIG. 8, blood is removed from a subject, e.g. a patient, in blood draw cycles. Blood removed in each cycle is processed batch wise in the system 1. Here, the processed blood is optionally collected in a container or so-called reservoir 13. Said processed blood or component is also returned to the subject 9 in cycles. Draw and return cycles are sequentially repeated during a selected period of time, whereby blood and/or blood components can for instance be cyclically removed from a subject, cyclically accumulated in the reservoir 13 and/or cyclically returned to the subject.

As can be understood from FIG. 8, blood can be removed from the subject 9 and can, e.g. via a manifold 16, preferably a controllable manifold, be conducted to the separator device 2. As mentioned before, an anticoagulant can be added to said blood, e.g. by means of an anticoagulant supply unit 8. The first component, substantially free of WBCs and platelets can then be depleted of RBC that have bound pathogens by means of the filter device 3. Downstream of the filter device 3, the first component substantially freed of RBC that have bound pathogens can then be combined with the second component, e.g. in a mixing unit 12 or mixing chamber, not shown in FIG. 8, but shown included in the embodiment of FIG. 9. As further can be understood from FIG. 8, the combined filtered first component and the second component can then be stored in the reservoir or container 13. After a while, the system 1 can stop drawing blood from the subject 9 and subsequently the system 1 may start feeding the filtered first component combined with the second component back to the subject 9. Thereto the manifold 16 may for instance be switched and/or a pump for drawing blood through the blood supply conduit 5 towards the separation device 2 can stop pumping and a pump for pumping blood or blood product from the reservoir 13 towards the subject 9 can start pumping said blood or blood product to the subject 9.

It is noted that system 1 may comprise one or multiple pumps (not shown). The pump or pumps can for instance be for drawing the blood or blood product, for instance from the subject 9 or patient or from an initial blood or blood product container 7, such as a blood bag, into and/or through the blood or blood product supply conduit 5 and/or to the separation device 2. One or more pumps may alternatively or additionally be for feeding the first component to the filter device 3 and/or for pumping and/or drawing the first component through the filter device 3. Alternatively or additionally, one or more pumps may be provided for pumping the second component from the separation device 2 and/or the filtered first component from the filter device 3 to a mixing unit 12, a storage reservoir 13, an administering device 6b, 6 and/or a subject. It is noted that one or more pumps can be arranged to perform multiple of the tasks mentioned above.

It is noted that for the purpose of clarity and a concise description features are described herein as part of the same or separate embodiments, however, it will be appreciated that the scope of the invention may include embodiments, for example methods and/or systems, having combinations of all or some of the features of embodiments described and/or shown, for example embodiments of methods and/or systems described and/or shown.

Further, it is noted that the invention is not restricted to the embodiments or examples described herein. It will be understood that many variants are possible.

For example, one or multiple of the conduits of the system may be provided as tubes, e.g. flexible tubes. Especially the blood or blood product supply conduit 5 and/or a supply conduit 14 for feeding cleaned blood or a cleaned blood product to e.g. a reservoir 13 or a subject 9, can be of flexible design. Said conduit or conduits may for instance be connected and/or releasably connectable to a housing 15 of the system 1.

As another example, the system 1 may be provided with one or more monitoring mechanism and/or control mechanism. For example, the system can comprise one or multiple pressure sensors, temperature sensors, air-bubble detectors, flow sensors, and/or other sensors or detectors. The system 1 may additionally be arranged to provide a warning signal or to even stop a process, e.g. a treatment process, being executed, if one or more variables being monitored exceed a predetermined threshold value. Alternatively or additionally, the system 1 may be arranged to control one or more of such variable. For instance thereto, the system may comprise means for adjusting one or more of such variables. For example, the system may be provided with a warmer and/or a cooler to warm and/or cool the blood, blood product and/or one or more separated components thereof. Hence, when for instance a too low temperature is detected, the system may control the warmer to warm the respective blood, blood product and/or component, e.g. in order to maintain a temperature substantially corresponding to a blood temperature. As another example, if, at a certain point in the system 1, the respective monitored flow rate drops below a certain threshold value, the system may for instance increase the output of a respective pump and/or may for instance adjust the amount of anticoagulant supplied to the blood or blood product. Further, the system 1 may comprise one or more input means, e.g. comprising a control panel, to operate at least parts of the system and/or to input desired threshold values.

Such and other variants will be apparent for the person skilled in the art and are considered to lie within in the scope of the invention as formulated in the appended claims.

Examples

Materials and Methods
Antibodies and Reagents

Anti-hBCAM (polyclonal goat IgG; catalog #AF148) was used from R&D systems (Minneapolis, USA). Anti-hCD147, (conjugate PE, Mouse IgG2A product code12-1472-41) was used form eBioscience. ICAM-4 (polyclonal, product code: H00003386-B01P) was used form Abnova. Anti-hCD163 (clone MAC2-158, conjugate PE) from *Trillium* Diagnostics, LLD was used. Final used blocking concentrations are: 0.2 mg/ml end concentration per $1\times10^{\wedge}7$ RBCs 30 min RT for anti-hLu/BCAM, 50 ug/ml end concentration per $1\times10^{\wedge}7$ RBCs 30 min RT for anti-ICAM-4, 20 ug/ml end concentration per $1\times10^{\wedge}7$ RBCs 30 min RT for anti-CD147.

Isolation and Storage of RBCs

Venous blood was collected from healthy donors, after obtaining informed consent. Blood studies were approved by the Sanquin Research institutional medical ethical committee in accordance with the standards laid down in the 1964 Declaration of Helsinki. Erythrocytes were isolated from fresh heparinized whole blood by centrifugation at 270 g for 15 min. After removing the platelet-rich plasma and the peripheral blood mononuclear cells, the erythrocytes were washed two times with saline-adenineglucose-mannitol (150 mmol/l NaCl, 1.25 mmol/l adenine, 50 mmol/l glucose, 29 mmol/l mannitol, pH 5.6) (SAGM) (Fresenius Kabi, The Netherlands), and resuspended in SAGM. Final cell concentration was determined with an Advia 2120 (Siemens Medical Solutions Diagnostics, Breda, The Netherlands). The erythrocytes were stored at 2 to 6° C. in a standard blood bank refrigerator.

Bacterial Binding to RBCs

For bacteria (or other microorganisms) to bind to RBCs, the bacteria first needed to become opsonized. This was done by incubating $1\times10^{\wedge}8$ bacteria with 200 ul of pooled serum of 18 AB+ healthy donors. After a washing step with Hepes buffer [132 mmol/l NaCl, 20 mmol/l HEPES (N-2-hydroxyethylpiperazine-N'-2-ethanesulfonic acid), 6 mmol/l KCl, 1 mmol/l MgSO4, 1.2 mmol/l $K_2HPO_4$, pH 7.4 (all from Sigma-Aldrich)] supplemented with 10 mmol/l glucose, 2 mmol/l CaCl2 and 0.5% HSA, the now opsonized bacteria were incubated with 0.1% PFA for 30 minutes followed by 2 times washing in Hepes buffer. Next, the opsonized bacteria were incubated with $1\times10^{\wedge}8$ RBCs for 30 min. again following a 2 step washing step. Some bacteria needed additional staining using a DNA-dye such as Hoechst to allow analysis of the bacterial binding percentage. RBCs were analysed and checked for bacterial binding % by flow cytometry using a LSR 11 (Becton Dickinson).

Monocyte Isolation Using Percoll Gradients and CD14+ Bead Isolation

Polymorphonuclear cells (PBMC) were isolated from heparinized peripheral blood from healthy donors by density gradient centrifugation using Percoll (Pharmacia). Monocytes were isolated from PBMC by MACS isolation using CD14 microbeads (Miltenyi Biotec). No stimulation was needed for bacterial transfer analysis.

Human Spleens

Spleens were collected from organ transplant donors without clinical signs of infection or inflammation. Written informed consent for organ donation was obtained according to national regulations regarding organ donation. Splenic tissue of the organ donor was obtained during transplantation surgery, as part of the standard diagnostic procedure for HLA-typing, and was transported in University of Wisconsin Fluid at 4° C. In case there was an excess of splenic tissue for diagnostic procedures, this excess of splenic tissue was used in an anonymous fashion for research in the present study, in accordance with the Dutch law regarding the use of rest material for research purposes.

Isolating Splenocytes

Splenocytes were isolated as described elsewhere (Nagelkerke et al. PLoS One. 2014 Feb. 11; 9(2)) by injecting a piece of spleen at several sites with collagenase buffer Collagenase CLSP 100 U/ml, DNAse, Deoxyribonuclease I, bovine recombinant 2 Kunitz Units/ml, Aggrastat 0.5 ug/mL, Glucose 1 mg/ml, Calcium Chloride 1 mM. Connective tissue was removed and the tissue was subsequently incubated in the collagenase buffer for 30 minutes at 37° C. Tissue was then filtered using a 100 μm filter. Subsequently, erythrocytes were lysed with an isotonic ammoniumchloride buffer for 5 minutes at 4° C., after which lysis buffer was washed away. To enrich for larger cells (monocytes/macrophages) elutriation is performed. Finally, cells were sorted directly from splenocytes stained for CD163 (a monocyte/macrophage marker) and auto fluorescence (specific for macrophages only) using a FACS Aria II machine (Becton Dickinson). Flow cytometric analysis was performed on an LSR II machine (Becton Dickinson).

Confocal Microscopy

In this method, monocytes or macrophages were isolated (as described) and plated on an Ibidi μ-Slide (Ibidi-Treat μ-Slide VI$^{04}$, 6 channels) made of a polymer that supports rapid adhesion. In each well 33 ul HEPES buffer [132 mmol/l NaCl, 20 mmol/l HEPES (N-2-hydroxyethylpiperazine-N'-2-ethanesulfonic acid), 6 mmol/l KCl, 1 mmol/l MgSO$_4$, 1.2 mmol/l K$_2$HPO$_4$, pH 7.4 (all from Sigma-Aldrich)] supplemented with 10 mmol/l glucose, 2 mmol/lCaCl2 and 0.5% HSA as the positive sample, or HEPES buffer supplemented with 10 mmol/l glucose, 2 mmol/l ethylene glycol tetraacetic acid (EGTA) (Sigma-Aldrich) and 0.5% HSA as the negative sample, was injected containing 80.000 monocytes/macrophages. Next, the ibidi-chamber was placed in an incubator for 30 min at 37° C. After 30 min, the ibidi-slide was positioned into the microscope stage and connected to one side of silicone tubing containing warm (e.g., 37° C.) flow-buffer (HEPES+), and a 20 ml syringe. NOTE: This tubing also contains an in-line Luer injection port (IBIDI, Catalog Number: 10820), which allows erythrocytes to be injected with a needle into a running experiment without stopping the flow and creating air bubbles. Next, the silicone exiting tube was connected to the other side of the ibidi-slide. The flow speed is adjusted to 0.2 dyn/cm$^2$, in accordance with physiological flow speed in splenic venules (0-1 dyn/cm$^2$). The pump will now push the flow-buffer from the syringe through the flow-chamber into the exiting tube. Fluorescent imaging of the erythrocytes (to which IC are bound) enable real-time determination of the extent of bacterial transfer to monocytes/macrophages. To quantify results in each bacterial transfer experiment the number of monocytes that had taken up one or more immune complexes, was counted throughout the whole length of an ibidi-slide when positioned in center of the well. Results were obtained using Differential Interference Contrast (DIC), GFP (488 nm) or Hoechst (405 nm) simultaneously using a confocal laser scanning microscope equipped with a climate chamber with a constant temperature at 37° C., 5% CO$_2$, and a 63× oil-objective. Data is analyzed using imaging software (Zen software 2008 and Zeiss LSM510 META; Carl Zeiss MicroImaging, Jena, Germany).

Depletion of RBCs Carrying an Opsonized Pathogen by the Use of a Non-Specific RBC Adhesion Molecule Binder.

RBCs to which bacteria (or other microorganisms) already have been bound are analysed by FACS to determine the pathogen binding percentage (as described earlier in materials and methods: Bacterial binding to RBCs). Next, the non-specific RBC adhesion molecule binder, in this case a Leukocyte Reduction Filter (LRF, BioR Blood filter, Fresenius Kabi, The Netherlands) is prewashed using 150 ml of SAGM. After which, 30 ml of SAGM is added containing the RBCs that have bound GFP+ or Hoechst+-expressing immune complexes. The filter is then washed twice with 150 ml of SAGM, all of which is collected, by centrifugation at 2500 RPM for 5 min. The obtained RBCs were analysed and checked for bacterial binding % by flow cytometry using a LSR II.

Isolation of Pathogens Bound by a Non-Specific RBC Adhesion Molecule Binder

To filter RBC-pathogen complexes from a suspension of RBC, the leucocyte reduction filter was washed first with 150 ml of SAGM (RBC storage solution). Then a suspension of 10$^8$ RBC containing RBC-pathogen complexes (prepared as described before in bacterial binding to RBC section) was applied to the filter. The percentage of RBC-pathogen complexes ranged per pathogen, *S. aureus* 39%, *E. faecalis* 12.5%, *C. albicans* 0.9%. After the application of the RBC, the filter was washed with 100 ml of SAGM. Subsequently, 100 ml of water was applied, in order to lyse the RBC, of which the first 50 ml was collected directly. The remaining 50 ml was left 10 minutes on the filter, in order to lyse the RBCs completely, and then obtained from the filter. The first 50 ml and the 50 ml of the second elution were both spun down, taken up in 100 ul of LB medium and plated. As a control, RBCs without any pathogens were also subjected to the same filter isolation procedure.

Etection of Pathogen Bound RBCs in Patient Samples

Blood from septic patients or from patients at risk of developing sepsis was first washed three times with PBS, and then stained by a DNA dye (Hoechst, 1:10.000, 15 min, RT), and washed twice. The sample was then analyzed by flow cytometry or confocal microscopy.

Statistical Analysis

Data was analyzed using Graphpad Prism 6 for Windows (GraphPad Software, La Jolla, Calif., USA). For statistical analysis between experimental groups, the Student's t-test was used. A two-sided p value of ≤0.05 was considered to be significant. Unless stated otherwise, a representative experiment out of at least three independent experiments is shown.

Results

Bacterial Binding is Dependent on Complement and CR1

Previously it has been shown that CR1 (also known as CD35 and the Knops blood group antigen) located on human Red blood cells (RBC) is the receptor that is responsible for binding newly formed immune complexes (IC). The RBC now acts as a shuttle, transferring the now bound IC throughout the whole body until it arrives at the liver or the spleen, where its cargo is selectively removed by macrophages of the Reticulo-Endothelial System (RES). To study this phenomenon, an assay was developed to monitor binding of opsonized GFP positive *S. aureus* to RBCs (FIG. 1A-B). To perform this assay, *S. aureus* was first incubated with serum and then incubated with RBCs for 30 min. RBCs were then analyzed by flow cytometry FIG. 1A represents the dot-plot of control RBCs (PI). P2 shows the % of GFP-positive RBCs or RBCs that have bound GFP-expressing opsonized *S. aureus* (FIG. 1B). To assess if other microorganisms are also able to bind to CR1 through complement, a series of experiments have been performed using the same protocol but with different microorganisms: *E. coli, C. albicans* and *S. Typhimurium*. All described microorganisms were indeed able to bind, although a variable binding percentage between different mirco-organisms is observed (FIG. 1C-1E) Next, to see if bacterial binding is indeed dependent on complement and CR1 another binding assay was performed (FIG. 1F). Bacteria were again opsonized using pooled serum prior to incubation with RBCs. Bacterial binding was measured as % of GFP-positive RBCs. In case *S. aureus* was treated with serum, a high increase in binding to RBCs was observed in comparison with non-opsonized bacteria. Moreover, a very low binding was detected when bacteria were pre-incubated with heat-inactivated (HI) serum. Bacterial binding was completely abolished when RBCs were pre-incubated with CR1 blocking antibody. These findings show that complement found in serum and CR1 on RBCs are necessary to ensure bacterial binding to RBCs.

Bacterial Transfer to Human Monocytes

In most of experiments, human monocytes isolated from whole blood were used instead of phagocytes from spleen. This is because splenic phagocytes are difficult to obtain and have reduced viability at the end of the sorting procedure and sample collection and preparation. It is generally accepted that monocytes isolated from whole blood are the phagocytic precursors of the cells of the RES and therefore a lot of their receptors are believed to be common. To visualize bacterial transfer to human monocytes, monocytes were isolated according to protocol and seeded on a glass plate and submerged in HEPES+ buffer. After an incubation period of 30 min in a 37° C. incubator, a small amount of RBCs to which opsonized GFP-expressing *S. aureus* was already bound, was pipetted on top of the monocytes. Using confocal microscopy to analyze the results, bacterial transfer to monocytes was clearly seen (FIG. 2). Additional experiments using different microorganisms (*E. coli, C. albicans, and S. Typhimurium*) to show IC transfer were also performed, all showing transfer of the microorganisms to human monocytes.

Bacterial Transfer Under Flow Conditions

To mimic a more lifelike situation, a flow system was developed in which the physiological flow speeds of the spleen are used, by means of confocal microscopy. Using this newly developed assay, but keeping all other features the same, bacterial transfer still occurred as normal (data not shown). In addition, a protocol was developed to isolate human splenocytes. Once isolated, splenic monocytes (CD163+) and macrophages (CD163+ and auto fluorescent) are selected to perform live imaging of bacterial transfer using GFP-expressing *S. aureus* (FIG. 3A-B) or *S. typhimurium* (C-D) bound to RBCs under flow conditions. Once again revealing bacterial transfer but this time to the phagocytes of the RES.

When looking at the flow assay results in more detail, it was noticed that just after bacterial transfer had occurred the RBC remains attached to the monocyte for a while. It was therefore hypothesized that RBC adhesion molecules are involved during the transfer process. RBC adhesion molecules are known to be calcium dependent. To test this hypothesis, several adhesion molecules were blocked under flow (FIG. 4). When using a blocking antibody against CD147 a significant reduction of about 50% is seen. When blocking ICAM-4 and Lu/BCAM, a similar reduction is shown. As an extra control, an antibody against an abundant antigen on the red blood cell membrane (anti-GPA) is used that is not involved in IAC. As expected, no reduction in bacterial transfer was seen (FIG. 4). Next, al three adhesion molecules were blocked at the same time, to see if this reduces bacterial transfer even further. No additional reduction is seen when all Abs are combined instead of using just one. Nevertheless, the data show that IAC is dependent on RBC adhesion molecules.

RBCs Carrying an Opsonized Pathogen are Depleted Using a Non-Specific RBC Adhesion Molecule Binder.

RBCs to which bacteria (or other microorganisms) already have been bound are firstly analysed by FACS to determine the immune complex (IC) binding percentage (as described earlier in materials and methods: Bacterial binding to RBCs). Due to inter-donor variation bacterial binding percentages (or other microorganisms) differ ranging from about 5%-40%, as is apparent from FIG. 1. After washing the filter (as described earlier in materials and methods: Depletion of RBCs carrying an opsonized pathogen.) all non-sticking RBCs are obtained and again analysed by FACS. As shown in FIG. 5, a nearly total pathogen reduction is seen in both cases of *C. albicans* (FIG. 5A; depleted from 6.7% to 0.5%) and *S. aureus* (FIG. 5B; depleted from 19.5% to 0.7%.

Isolation of Pathogens Bound by a Non-Specific RBC Adhesion Molecule Binder

RBCs to which *S. aureus, E. faecalis* or *C. albicans* were bound were depleted using a BioR blood filter (Fresenius Kabi). Subsequently, RBC were lysed and the resulting samples containing the pathogens were plated. The results are shown in FIG. 10B-D. All three pathogens could be successfully plated. FIG. 10 A shows a control of RBC without pathogens.

Detection of Pathogen Bound RBCs in Patient Samples

The percentage of RBC-pathogen complexes in blood samples from septic patients ranged from 1 to 1.7% in the patients tested (table 1). Patients suffered from or were developing sepsis, e.g. induced by *K. pneumoniae* (patient 2) or *E. coli* (patient 3). In healthy controls no RBC-pathogens complexes were observed. The samples of patients 1 and 3 showed a positive blood culture.

TABLE 1

| Sample | % RBC-pathogen complexes |
| --- | --- |
| Patient 1 | 1 |
| Patient 2 | 1.5 |
| Patient 3 | 1.7 |
| Healthy control 1 | not detectable |
| Healthy control 2 | not detectable |
| Healthy control 3 | not detectable |

FIG. 10 show the microscopic analysis and flow cytometric analysis for a patient suffering from a *K. pneumoniae* induced sepsis and a patient suffering from a *E. coli* induced sepsis. FIG. 11 shows the flow cytometric analysis of one patient developing a *K. pneumoniae* induced sepsis. The percentage of RBC-pathogen complexes in a sample obtained from this patient was 1.5% (FIG. 11B). Of note, this sample was taken 2 days before the patient had a positive blood culture and was diagnosed with sepsis. The presence of RBC-pathogen complexes was confirmed by confocal microscopy analysis (FIG. 1B) and a positive blood culture 2 days later.

The invention claimed is:

1. A method for the removal of a pathogen selected from the group consisting of a bacterium, a virus, and a fungus from blood or a blood product comprising red blood cells, said method comprising:

(a) separating said blood or blood product into at least two components, (i) a first component comprising red blood cells (RBCs) and substantially free of white blood cells (WBCs) and platelets, and (ii) a second component comprising WBCs and platelets and substantially free of RBCs;

(b) contacting said first component with a leukocyte reduction filter or with a support selected from the group consisting of a filter, microfibers, microparticles, beads, microspheres, an array, glass slides and microscope slides, said support comprising a non-specific RBC adhesion molecule binder to substantially deplete the first component of RBCs that have bound the pathogen, wherein said non-specific RBC adhesion molecule binder is a polymer or a mixture of two or more polymers that binds to adhesion molecules that become activated and are expressed on RBCs and is selected from one or more of the group consisting of polyester, polyurethane, cellulose, nylon, nitrocellulose, polypropylene, polyethylene terephthalate (PET), polyimide (PI), polyvinyl alcohol (PVA), and polyvinylidene fluoride (PVDF), and mixtures thereof; and (c) optionally combining said first component that is substantially depleted of RBCs that have bound the pathogen and said second component.

2. The method of claim 1, further comprising storing said first component that is substantially depleted of RBCs that have bound the pathogen and said second component.

3. A method for the removal of a pathogen selected from the group consisting of a bacterium, a virus and a fungus from blood of a patient in need thereof comprising:

(a) withdrawing the blood from said patient;

(b) separating said blood into at least two blood components, (i) a first component comprising red blood cells (RBCs) and substantially free of white blood cells (WBCs) and platelets, and (ii) a second component comprising WBCs and platelets and substantially free of RBCs;

(c) contacting said first component with leukocyte reduction filter or with a support selected from the group consisting of a filter, microfibers, microparticles, beads, microspheres, an array, glass slides and microscope slides, said support comprising a non-specific RBC adhesion molecule binder to substantially deplete the first component of RBCs that have bound the pathogen, wherein said non-specific RBC adhesion molecule binder is a polymer or a mixture of two or more polymers that binds to adhesion molecules that become activated and are expressed on RBCs and is selected from one or more of the group consisting of polyester, polyurethane, cellulose, nylon, nitrocellulose, polypropylene, polyethylene terephthalate (PET), polyimide (PI), polyvinyl alcohol (PVA), and polyvinylidene fluoride (PVDF), and mixtures thereof;

(d) optionally combining said first component that is substantially depleted of RBCs that have bound the pathogen and said second component; and (e) returning said first component that is substantially depleted of RBCs that have bound the pathogen and said second component to said patient.

4. The method of claim 3, wherein the patient has sepsis.

5. The method of claim 3, wherein said blood is continuously withdrawn from said patient and said first component that is substantially depleted of RBCs that have bound the pathogen and said second component are continuously returned to said patient.

6. The method of claim 1, wherein said pathogen is a bacterium or a fungus selected from the group consisting of *Staphylococcus aureus, Salmonella typhimurium, Escherichia coli, Candida albicans, Enterococcus faecalis* and *Bacillus subtilis*.

7. The method of claim 1, wherein said first component that is substantially depleted of RBCs that have bound the pathogen and said second component are combined.

8. A method for the removal of a pathogen selected from the group consisting of a bacterium, a virus, and a fungus from a blood product comprising red blood cells, wherein the blood product is substantially free of white blood cells and platelets, said method comprising contacting said blood product with a non-specific RBC adhesion molecule binder, wherein said non-specific RBC adhesion molecule binder comprises a leukocyte reduction filter or a polymer or a mixture of two or more polymers that binds to adhesion molecules that become activated and are expressed on RBCs the polymer or mixture of two or more polymers being selected from one or more of the group consisting of polyester, polyurethane, cellulose, nylon, nitrocellulose, polypropylene, polyethylene terephthalate (PET), polyimide (PI), polyvinyl alcohol (PVA), and polyvinylidene fluoride (PVDF), and mixtures thereof.

9. The method according to claim 8, wherein said polymer or a mixture of two or more polymers are coated on beads.

10. The method according to claim 8, further comprising combining said blood product with a second blood product comprising white blood cells and platelets, wherein the second blood product is substantially free of red blood cells.

11. The method of claim 1, wherein the support is beads coated with the non-specific RBC adhesion molecule binder.

12. The method of claim 3, wherein the support is beads coated with the non-specific RBC adhesion molecule binder.

* * * * *